United States Patent
Lee

(10) Patent No.: US 10,859,170 B2
(45) Date of Patent: Dec. 8, 2020

(54) PINCH VALVE FOR A URINARY DRAINAGE SYSTEM

(71) Applicant: ROYAL UNITED HOSPITALS BATH NHS FOUNDATION TRUST, Bath (GB)

(72) Inventor: Siu Man Lee, Bath (GB)

(73) Assignee: ROYAL UNITED HOSPITALS BATH NHS FOUNDATION TRUST, Bath (GB)

( * ) Notice: Subject to any disclaimer, the term of this patent is extended or adjusted under 35 U.S.C. 154(b) by 53 days.

(21) Appl. No.: 15/751,642

(22) PCT Filed: Aug. 2, 2016

(86) PCT No.: PCT/GB2016/052376
§ 371 (c)(1),
(2) Date: Feb. 9, 2018

(87) PCT Pub. No.: WO2017/025715
PCT Pub. Date: Feb. 16, 2017

(65) Prior Publication Data
US 2018/0245699 A1    Aug. 30, 2018

(30) Foreign Application Priority Data
Aug. 12, 2015    (GB) .................................. 1514322.5

(51) Int. Cl.
*F16K 7/04*    (2006.01)
*F16K 7/06*    (2006.01)
(Continued)

(52) U.S. Cl.
CPC ............ *F16K 7/045* (2013.01); *A61F 5/4405* (2013.01); *A61M 27/00* (2013.01); *F16K 7/06* (2013.01); *A61M 39/28* (2013.01)

(58) Field of Classification Search
CPC ........... F16K 7/045; F16K 7/06; A61F 5/4405
(Continued)

(56) References Cited

U.S. PATENT DOCUMENTS 2,092,401 A * 9/1937 Miller ................. A61M 39/286
251/7
3,203,421 A * 8/1965 Bialick ................. A61F 2/0054
128/885
(Continued)

FOREIGN PATENT DOCUMENTS

EP    1 211 445 A1    6/2002
EP    1211445 A1    6/2002
(Continued)

OTHER PUBLICATIONS

Assistive Designs, "Pinch Style Emptier", AssistiveDesigns.com, [online], Available from: http://www.assistivedesigns.com/emptiers.data/components/pinch.php [Accessed Jan. 28, 2016].
(Continued)

*Primary Examiner* — Umashankar Venkatesan
(74) *Attorney, Agent, or Firm* — Leason Ellis LLP

(57) ABSTRACT

A pinch valve for a urinary drainage system comprises a tube attachment part for attaching the pinch valve to a tube of the urinary drainage system so that the tube is received in a tube receiving region of the pinch valve; a first pinch part and a second pinch part having the tube receiving region therebetween, wherein the first pinch part is moveable towards the second pinch part for compressing a tube received in the tube receiving region against the second pinch part; and an actuator operable to move the first pinch part; wherein the tube attachment part is openable so that the tube is receivable in the tube receiving region, and closeable so that the tube is retained in the tube receiving region.

11 Claims, 9 Drawing Sheets

(51) Int. Cl.
    *A61M 27/00* (2006.01)
    *A61M 39/28* (2006.01)
    *A61F 5/44* (2006.01)
(58) Field of Classification Search
    USPC .......................................................... 251/7, 8
    See application file for complete search history.

(56) References Cited

U.S. PATENT DOCUMENTS

| | | | | |
|---|---|---|---|---|
| 4,337,791 | A * | 7/1982 | Tech | A61M 39/286 |
| | | | | 137/556 |
| 4,425,116 | A * | 1/1984 | Bilstad | A61M 39/285 |
| | | | | 137/595 |
| 4,559,045 | A * | 12/1985 | Danby | A61M 39/28 |
| | | | | 604/250 |
| 4,653,719 | A * | 3/1987 | Cabrera | F16K 11/027 |
| | | | | 251/4 |
| 5,092,856 | A * | 3/1992 | Johnston | A61M 39/28 |
| | | | | 604/249 |
| 5,219,327 | A * | 6/1993 | Okada | A61M 5/14228 |
| | | | | 128/DIG. 12 |
| 5,814,004 | A * | 9/1998 | Tamari | F04B 43/1253 |
| | | | | 604/6.1 |
| 5,924,852 | A * | 7/1999 | Moubayed | A61M 5/14228 |
| | | | | 417/474 |
| 5,964,583 | A | 10/1999 | Danby | |
| 6,261,269 | B1 | 7/2001 | Lecuyer | |
| 6,942,473 | B2 * | 9/2005 | Abrahamson | A61M 5/14228 |
| | | | | 417/474 |
| 7,559,525 | B2 * | 7/2009 | Grimes | F16K 7/061 |
| | | | | 251/8 |
| 7,571,889 | B2 * | 8/2009 | Miyahara | A61M 39/287 |
| | | | | 251/4 |
| 2002/0173758 | A1 | 11/2002 | Whiting | |
| 2003/0189309 | A1 | 10/2003 | Schmaltz | |

FOREIGN PATENT DOCUMENTS

| | | |
|---|---|---|
| WO | WO 2011/116393 A1 | 9/2011 |
| WO | WO 2017/003937 A1 | 1/2017 |

OTHER PUBLICATIONS

Lee, S.M., et al., "Design and development of a novel automatic valve system for long-term catheterized urinary incontinence patients", Proceedings of the Institution of Mechanical Engineers, Part H: J. Engineering in Medicine, vol. 221 2007, pp. 665-676.

Examination Report under Section 18(3) issued by the Intellectual Property Office in the United Kingdom dated Mar. 18, 2020 under Application No. GB 1514322.5.

Australian Examination Report, dated Jul. 27, 2020; Application No. 2016306004.

Great Britain Examination Report, dated Jun. 25, 2020; Application No. GB1514322.5.

* cited by examiner

PINCH VALVE FOR A URINARY DRAINAGE SYSTEM

CROSS-REFERENCE TO RELATED APPLICATIONS

This application is a U.S. National Stage Application under 35 U.S.C. § 371 of International Patent Application No. PCT/GB2016/052376, filed Aug. 2, 2016, which claims priority to Great Britain Application No. 1514322.5, filed Aug. 12, 2015, which are hereby incorporated by reference in their respective entireties.

FIELD OF THE INVENTION

The present invention relates to a pinch valve for a urinary drainage system.

BACKGROUND OF THE INVENTION

A urinary drainage system is a system (device or apparatus) that is used for draining urine from a urinary bladder, typically the urinary bladder of a person.

A urinary drainage system typically consists of a urinary catheter for draining fluid from the urinary bladder and a urine collector, such as a urine drainage bag, for collecting the urine drained by the urinary catheter.

The urinary catheter may be a urethral catheter, which is positioned in a patient by being passed up through the patient's urethra to access the urinary bladder. Alternatively, the urinary catheter may be a suprapubic catheter, which is inserted into the patient's urinary bladder through the abdominal wall just above the pubic bone, i.e. via a surgically produced suprapubic track.

A urinary catheter is typically a tube, usually made of silicone, which at a first end has two eyeholes to drain the urine from the urinary bladder and an inflatable balloon to retain its position in the urinary bladder, and which at a second end is open, allowing the user to connect it to a urine collection bag.

Urinary drainage systems may be used for the short-term, for example during surgery or a short hospital stay, in which case the urinary catheter may only need to be in-situ for a short period of time. For example, approximately one out of every four hospitalised patients receives an indwelling catheter.

However, in some cases it is necessary for a urinary drainage system to be used for the long term, for example where a patient suffers from urinary incontinence, in which case the urinary catheter may need to be in-situ for a long time. It is estimated that approximately 9 percent of the population worldwide suffer from urinary incontinence, which equates to over three million urinary incontinence patients in the UK alone. Apart from situations where the condition can be surgically or medically treated, urinary catheters are commonly used for management of urinary incontinence.

However, there are a number of problems associated with the use of urinary catheters, particularly when they are used for the long term, e.g. to treat urinary incontinence.

Patients who use urinary catheters for the long term often experience encrustation problems. This is a crystal build-up in the urine, such as a calcium phosphate and/or magnesium ammonium phosphate hexahydrate. It is believed that encrustation is closely related to urinary tract infection by the bacteria *Proteus mirabilis*, which increases the alkalinity of the urine and encourages the formation of the encrustation. Encrustation often leads to urinary catheter blockage as the accumulating crystals will eventually fill up the eyehole and the lumen of the urinary catheter.

The conventional way of using a urinary catheter in commercially available urinary drainage systems is to allow the urine to be continuously draining, so that urine can freely drain from the urinary bladder to the urine drainage bag through the urinary catheter at all times. However, with this arrangement the flowrate of the urine is so low it is difficult to differentiate between a normal flow and the results of a blockage. Hence, the patient's urinary catheter may block at any time without the patient's knowledge until the overfilled bladder causes reflux in the kidneys. In such situations, the patient will require emergency medical attention either in hospital or in the home. This leads to a considerable financial burden.

To address this problem, intermittent drainage of the urine has been proposed and demonstrated using a manually operated catheter valve in-line between the urinary catheter and the urine drainage bag. The manually operated catheter valve can be operated by the patient when required to drain the urine from the urinary bladder into the urine collector. Operation of the valve is typically achieved by a push button or by flipping a lever.

Such intermittent drainage of the urine has been shown to improve encrustation resistance, extending the service lifetime of a conventional urinary catheter by up to a factor of four. With such a system the patient may also be less susceptible to infection and the catheter can also provide bladder training (filling and emptying) which would allow the continuous exercise of the bladder wall tissue. This would help to maintain the urine collection function of the bladder and may assist the rehabilitation process. Furthermore, such a system can provide an early warning of catheter blockage, because if the flow rate is substantially reduced or even stopped when the valve is opened, the patient can immediately seek assistance before the problem becomes critical.

The present inventor has realised that intermittent drainage of urine, and the associated benefits described above, can be better achieved using an automatic catheter valve, i.e. a catheter valve in which operation (opening and closing) of the catheter valve occurs automatically. Using such an automatic catheter valve provides a urinary drainage system that is more convenient to the patient, and which is also better suited to patients with limited manual dexterity who are not able to operate a manually operated catheter valve, or patients who are likely to forget to manually operate the valve.

An automatic catheter valve for use in a urinary drainage system is described in the article "*Design and development of a novel automatic valve system for long-term catheterized urinary incontinence patients*" by S. M. Lee et al published in the Proceedings of the Institution of Mechanical Engineers, volume 221, part H: journal of Engineering in Medicine, pages 665 to 676, published 9 May 2007. The whole contents of that article are incorporated herein by reference. In the following, the automatic catheter valve described in that article is referred to as "the known automatic catheter valve".

The external appearance of a prototype of the known automatic catheter valve is shown in FIG. 1, and a schematic of the internal mechanism of the known automatic catheter valve is shown in FIG. 2.

As shown in FIG. 1, the valve 1 is an in-line valve having first 3 and second 5 cone connectors for connecting the valve 1 in line between two tubes of a urinary drainage system, typically between an output end of a urinary catheter and an input end of a urine collection bag.

FIG. 2 shows a schematic illustration of the internal mechanism of the valve 1 for stopping and allowing drainage of urine into the urine drainage bag through the valve 1 (i.e. closing and opening the valve). As shown in FIG. 2, the valve has an internal tube 7 which is fixed between the first 3 and second 5 cone connectors in fluid communication with the first 3 and second 5 cone connectors, so that urine entering the valve 1 via the first cone connector 3 passes through the internal tube 7 to exit the valve 1 via the second cone connector 5, which will typically be connected to a urine drainage bag.

The valve 1 is a pinch valve, in which flow of fluid through the valve 1 can be prevented by pinching the internal tube 7 to substantially prevent fluid flow through the internal tube 7.

The valve is closed by a valve shuttle 9 being moved linearly to compress the internal tube 7 against a stop 11 on an opposite side of the internal tube 7 to the valve shuttle 9. The valve shuttle 9 is moved linearly by an electric motor 13 turning a threaded screw 15. The valve shuttle 9 is threadedly engaged with the threaded screw 15 but prevented from rotating with the threaded screw 15, so that rotation of the threaded screw 15 by the motor 13 causes linear movement of the valve shuttle 9. Thus, linear movement of the valve shuttle 9 in either direction can be achieved by operating the electric motor in either rotational direction.

FIG. 2(a) shows the valve 1 closed, wherein the valve shuttle 9 has been moved linearly by operation of the motor 13 to completely squash the internal tube 7 against the stop 11 at the pinching point so that fluid cannot pass through the internal tube 7 at the pinching point. As shown in FIG. 2(a), in this configuration urine accumulates in the internal tube 7 above the pinching point. The internal tube 7 contains the urine to its full diameter above the pinching point but is collapsed at the pinching point.

FIG. 2(b) shows the valve 1 open, wherein the valve shuttle 9 has been linearly moved away from the stop 11 by operation of the motor 13 so that the internal tube 7 expands to its full diameter at the pinching point due to the pressure from the urine flow. In this configuration, urine is discharged through the valve 1.

FIG. 2(c) shows the valve 1 open after the urine has drained through the valve 1. Once the urine has drained, the size of the internal tube 7 is reduced due to the removal of the pressure from the urine.

The internal tube 7 of the valve 1 is a soft, flexible tube. Therefore, the valve shuttle 9 does not have to overcome any significant stiffness of the internal tube 7 in order to close the valve 1, which means the valve 1 can operate with low actuating energy. Furthermore, it is believed that the continuous flexing of the internal tube 7 could prevent crystallised material from adhering to the inner surface of the internal tube 7, further increasing the resistance to encrustation of the valve 1.

Operation of the valve 1 is controlled automatically by an integral microcontroller. Specifically, the integral microcontroller is programmed to open the valve 1 at predetermined time intervals, ranging from two to four hours, for short periods (e.g. 10 minutes) to empty the patient's bladder. However, the valve 1 also has an integral manual override allowing the user to open the valve 1 at any time to drain urine without causing disruption to the regularity of the predetermined opening time interval. The manual override comprises a magnetic reed switch module which can be activated to open the valve 1 by a user bringing a magnet close to the magnetic reed switch.

Other features of the known automatic catheter valve are described in the article, and are not repeated here for reasons of conciseness.

SUMMARY OF THE INVENTION

While the known automatic catheter valve described above has numerous advantages over existing commercial valves, the present inventor has realised that improvements can be made to the known automatic catheter valve, and indeed more generally to other valves for urinary drainage systems.

The present invention is concerned with several improvements of a valve for use in a urinary drainage system, which improvements may be used alone, or in combination.

In some embodiments, the present invention may relate to an improvement of the known automatic catheter valve described above, and therefore the present invention may have any one or more of the features of the known automatic catheter valve described above.

Firstly, the present inventor has realised that the known automatic catheter valve may still suffer from encrustation, for example due to infection by the bacteria *Proteus mirabilis*. Specifically, the present inventor has realised that the first and second cone connectors of the known automatic catheter valve are likely areas for the formation of encrustation, because these components come into direct contact with urine draining through the valve, and therefore into direct contact with bacteria in the urine. Such cone connectors are also used in other valves for urinary drainage systems. As mentioned above, the formation of encrustation is a significant problem for valves for urinary drainage systems, reducing the lifetime and reliability of the valves and representing a significant health risk to the patient.

The present inventor has realised that the problem of encrustation may be further reduced, and the reliability and lifespan of the valve further improved, by further isolating the valve from the urine draining through the valve.

The present inventor has realised that this can be achieved by providing a pinch valve that can be arranged around an existing tube of a urinary drainage system, such as a tube of a urinary catheter or a tube of a urine drainage bag, so that the pinch valve is operable to directly pinch the existing tube of the urinary drainage system. Thus, the entirety of the valve is isolated from the urine flowing through the valve, so that no additional encrustation of the urinary drainage system is caused by the inclusion of the valve in the system. Specifically, such a valve does not require the cone connectors of the known automatic catheter valve, which are believed to generate additional encrustation, because it is not connected 'in-line' in the flow path of the urine. Instead, the valve may be a "clip-on" valve.

Therefore, at its most general the present invention relates to a pinch valve for a urinary drainage system wherein the pinch valve is arrangeable around an existing tube of the urinary drainage system so that the pinch valve is operable to pinch the existing tube of the urinary drainage system.

According to a first aspect of the present invention there is provided a pinch valve for a urinary drainage system comprising:

a tube attachment part for attaching the pinch valve to a tube of the urinary drainage system so that the tube is received in a tube receiving region of the pinch valve;

a first pinch part and a second pinch part having the tube receiving region therebetween, wherein the first pinch part is moveable towards the second pinch part for compressing a tube received in the tube receiving region against the second pinch part; and an actuator operable to move the first pinch part.

Thus, the pinch valve according to the first aspect of the present invention can be attached to an existing tube of the urinary drainage system, for example a tube of a urinary catheter or a tube of a urine drainage bag, so that the tube is received in the tube receiving region of the pinch valve. The first pinch part can then be moved by operating the actuator so that the first pinch part compresses the tube against the second pinch part, thereby pinching the tube so that fluid flow through the tube is substantially prevented (i.e. the valve is closed).

Since the pinch valve acts to pinch the existing tube of the urinary drainage system, the pinch valve does not come into contact with the urine flow. Thus, the bio-isolation of the urinary drainage system is maintained, reducing the risk of bacteria entering the urinary drainage system and causing a urinary tract infection.

Furthermore, since the pinch valve is not connected in-line with a catheter or urine drainage bag of the urinary drainage system, it does not have connectors such as the cone connectors used in the known automatic catheter valve for connecting the known automatic catheter valve in-line. Thus, the pinch valve according to the first aspect of the present invention does not cause additional encrustation to occur in the urinary drainage system, and therefore has an increased reliability and lifespan relative to the known automatic catheter valve.

The pinch valve can be attached to the tube of the urinary drainage system by the tube attachment part. Thus, the pinch valve can easily be integrated into an existing urinary drainage system, i.e. a urinary drainage system in situ on a patient, without having to remove or disassemble the urinary drainage system.

The pinch valve according to the first aspect of the present invention may have any one, or, to the extent they are compatible, any combination of the following optional features.

The pinch valve is preferably portable, i.e. it is small and light enough to be carried around by a patient as part of their urinary drainage system.

The pinch valve is preferably stand alone, i.e. it doesn't require any other parts to function, for example a separate power supply.

The pinch valve may be attached to the tube of the urinary drainage system by the tube attachment part while some or all of the urinary drainage system is in-situ in the patient. For example, the pinch valve may be attached to a tube of a urinary catheter adjacent to a first end of the urinary catheter, wherein the second end of the urinary catheter has been inserted into a patient's urinary bladder to drain urine from the urinary bladder (i.e. while the urinary catheter is an indwelling catheter).

The term pinch valve means that the valve operates, i.e. is closed, by pinching or compressing the tube to prevent or significantly restrict flow of fluid through the tube at the pinch point.

In practice, the first and second pinch parts may be any parts that act to pinch or compress the tube when the valve is closed. One or both of the first and second pinch parts may be a flat surface against which the tube is compressed.

The term pinching means compressing between two surfaces, edges or points so as to prevent or significantly restrict fluid flow through the tube.

The first pinch part may be moved directly towards the second pinch part, i.e. linearly towards the second pinch part along a line connecting the first pinch part and second pinch part (e.g. in a forward direction). Alternatively, the first pinch part may be moved indirectly towards the second pinch part, for example in a sideways direction, or along a curved path, or along an angled path.

A urinary drainage system may be a combination of a urinary catheter for draining fluid from a urinary bladder and a urine collector for collecting fluid drained by the urinary catheter. The term apparatus or part may be used instead of the term system.

The tube attachment part may attach the pinch valve to the tube of the urinary drainage system by releasably retaining or securing the tube in the tube receiving region.

The tube attachment part may be configured for being arranged around the tube of the urinary drainage system.

The tube attachment part may comprise a tube receiving compartment, or a tube receiving housing.

The tube receiving region may be contained inside, or housed within, the tube attachment part. For example, the tube receiving region may be a space, void, channel or lumen within the tube attachment part.

The tube attachment part may be a clip-on part for clipping the pinch valve on to the tube of the urinary drainage system.

Attaching the pinch valve to the tube may mean fixing or securing the pinch valve to the tube.

The pinch valve is preferably detachable from the tube of the urinary drainage system after it has been attached to the tube of the urinary drainage system by the tube attachment part. Thus, the pinch valve can be attached to, and detached from, the same or different tubes of urinary drainage systems more than once.

The feature that the pinch valve is removable from the tube of the urinary drainage system may facilitate cleaning and/or maintenance of the pinch valve. For example, when the pinch valve has been removed from the tube of the urinary drainage system it may be possible to easily clear debris from around the pinch valve, for example from around the first and second pinch parts, that may otherwise prevent the pinch valve from working correctly.

The feature that the pinch valve is removable from the tube of the urinary drainage system may be advantageous if the pinch valve becomes stuck in the closed position with the tube pinched between the first and second pinch parts, for example where the actuator becomes inoperable for some reason. In this situation, urine would continue to build up above the pinch point and could reflux into the kidney of the patient, causing injury to the patient. Where the pinch valve is removable, the pinch valve can simply be removed from the tube (e.g. by opening or disengaging the tube attachment part) to release the pinching pressure on the tube to allow liquid to drain through the tube. The pinching force/pressure applied to the tube when the valve is closed may be predetermined so that a user is able to pull the valve away from the tube to remove the valve from the tube in an emergency when the tube is pinched between the first and second pinch parts.

The tube attachment part may be configured for attaching the pinch valve to a tube of a urinary catheter, or for attaching the pinch valve to a tube of a urine collector such as a urine drainage bag. In practice, the tube attachment part may attach the pinch valve to a portion of a urinary catheter adjacent an output end of the urinary catheter through which urine drains out of the urinary catheter, or a portion of a urine drainage bag adjacent an input end of the urine drainage bag through which urine drains into the urine drainage bag.

The tube attachment part may have an opening through which the tube of the urinary drainage system is inserted so that it is received in the tube receiving region. The opening may be along a side of the tube receiving region, so that the tube is inserted into the tube receiving region sideways. The opening may be openable and closeable.

The actuator may be any part that is used to move the first pinch part.

The actuator may be manually powered or powered by a power supply such as a battery.

The actuator may be manually operated, i.e. operates in response to an action by a user, or may operate automatically, i.e. operates without an action by a user.

The actuator may comprise a motor, which may be an electrical motor, for example with a corresponding electrical power source such as a battery.

The tube attachment part may be openable so that the tube is receivable in the tube receiving region, and closeable so that the tube is retained in the tube receiving region. Thus, the pinch valve may be attached to, connected to, or arranged around the tube of the urinary drainage system by the tube being received in the tube receiving region when the tube attachment part is open and then retained in the tube receiving region by the tube attachment part being closed.

The tube attachment g part may have a moveable part that is moveable to open and close the tube attachment part. The moveable part may be movable by a user of the pinch valve, e.g. it may be accessible at an external surface of the pinch valve.

The moveable part may be a moveable to uncover the tube receiving region to open the tube attachment part and to cover the tube receiving region to close the tube attachment part.

The moveable part may be a movable panel, moveable sidewall, moveable lid, or a movable part of a housing of the tube attachment part.

The moveable part may be detachable from the pinch valve. In other words, the moveable part may be a discrete part that can be disconnected from the pinch valve, such as a removable panel or sidewall.

Alternatively, the moveable part may be hinged to the pinch valve, so that the tube attachment part can be opened or closed by moving the moveable part around the hinge. For example, the moveable part may be a hinged flap, panel or lid.

The pinch valve may comprise a releasable latch for releasably securing the moveable part in place. This may prevent unwanted movement of the moveable part.

The tube receiving region may comprise an elongate channel for receiving the tube. Thus, the tube can be received in the tube receiving region by being positioned in the channel. The movable part may be movable to cover or uncover an elongate side of the elongate channel. The tube may be moved sideways into the channel through the side of the channel to be received in the tube receiving region.

The present inventor has also realised that it is advantageous to prevent movement of the tube within the tube receiving region. For example, it is advantageous to ensure that the tube remains properly located in the tube receiving region between the first and second pinch parts, so that the pinching action of the pinch valve works properly to pinch the tube. This may be particularly important where the pinch valve may be used with more than one type of tube having different diameters.

Thus, the pinch valve may comprise tube engaging means configured to engage a tube received in the tube receiving region. Engaging the tube may mean gripping, holding or otherwise positioning, locating, restraining or retaining the tube in the tube receiving region.

The tube engaging means may be part of the tube attachment part, or connected to, or housed within, the tube attachment part.

The tube engaging means is different (i.e. distinct or separate) to the first and second pinch parts.

The tube engaging means may be configured to hold the tube in a predetermined position in the tube receiving region so that the tube is correctly positioned and compressed between the first and second pinch parts when the valve is closed.

The tube engaging means may comprise tube gripping means for gripping the tube.

The tube engaging means may comprise tube clamping means for clamping the tube.

The tube engaging means may comprise opposed first and second engaging parts configured to engage the tube therebetween.

The tube engaging means may be configured to engage the tube therebetween only when the tube attachment part is closed.

The tube engaging means may be adaptable to engage tubes of different shapes and/or sizes. For example, part or all of the tube engaging means may be resiliently deformable so that the tube engaging means can adapt to the specific shape and/or size of the tube.

Part of all of the first engaging part and/or the second engaging part may resiliently deformable.

Where the tube attachment part has the moveable part for opening and closing the tube attachment part, the first engaging part may be attached to the moveable part. Thus, the tube may be engaged between the first and second engagement parts simultaneously with the tube attachment part being closed.

More generally, some or part of the tube engaging means may be arranged on the moveable part, so that the tube is engaged by the engaging means simultaneously with the tube attachment part being closed.

There may be provided a urinary drainage system comprising the pinch valve according to the first aspect of the present invention, optionally with any one or more of the optional features described above, wherein the pinch valve is attached to a tube of the urinary drainage system by the tube attachment part with the tube received in the tube receiving region.

The urinary drainage system may comprise a urinary catheter, and the pinch valve may be attached to a tube of the urinary catheter by the tube attachment means with the tube of the urinary catheter received in the tube receiving region. For example, a part of the urinary catheter adjacent an output end of the urinary catheter from which urine drains from the urinary catheter may be received in the tube receiving region.

The urinary drainage system may comprise a urine collector, and the pinch valve may be attached to a tube of the urine collector by the tube attachment means with the tube of the urine collector received in the tube receiving region. For example, a part of the urine collector adjacent an input end of the urine collector through which urine drains into the urine collector may be received in the tube receiving region. The urine collector may be a urine drainage bag.

Of course, in practice only a part or section of a tube of the urinary catheter or urine collector will actually be received in the tube receiving region.

The tube of the urinary drainage system may have a reduced wall-thickness portion having a reduced wall-thickness; and the reduced wall-thickness portion may be received in the tube receiving region. In other words, the wall thickness of the tube of the urinary drainage system (e.g. the tube of the urinary catheter or urine collector) may have thinner walls over a section or part of its length, and the section or part having the thinner walls may be received in the tube receiving region. This is advantageous because the thinner walled part of the tube will be more flexible/softer and therefore will be easier for the pinch valve to pinch. Thus, the actuating energy and/or the power consumption and/or the size of the pinch valve can be reduced.

The tube may have a locator attached thereto for locating the pinch valve on the tube; and the pinch valve may have a locator engaging part for engaging the locator to locate the pinch valve on the tube.

For example, where the tube has a thin walled section as described above, the locator may be positioned to ensure that the pinch valve is positioned relative to the tube so that the thin walled section is received in the tube receiving region.

The interaction or engagement between the locator and the locator engaging part may prevent movement of the tube in the tube receiving region and/or may ensure that the tube is correctly positioned, arranged or located within the tube receiving region relative to the first and second pinch parts.

The locator and the locator engaging part may have complementary shapes so that the locator engaging part is engagable with the locator only in one or more discrete rotational orientations of the locator engaging part. Thus, the locator and locator engaging part may enable control of the rotational orientation of the pinch valve relative to the tube as well as the absolute position of the pinch valve relative to the tube.

The engagement between the locator and the locator engaging part may be such to prevent rotation of the tube within the tube receiving region.

The locator may comprise a protrusion on the tube; and the locator engaging part may comprise a corresponding recess for engaging the protrusion.

The locator may be formed as part of the tube, for example moulded together with the tube. In other words, the urinary catheter or the urine collector may be specially designed to include a locator in an appropriate position for use with the pinch valve.

Alternatively, the locator may be formed separately and then attached or secured to the tube. An advantage of forming the locator separately and then attaching it to the tube is that the locator can be attached to existing tubes, for example existing urinary catheters or urine collectors, allowing the pinch valve of the present invention to be used with existing urinary drainage systems (i.e. retro-fit to an existing tube).

The locator may comprise a band around the tube. For example a band formed with the tube or a band attached, positioned or arranged around an outer surface of the tube.

For example, the band may comprise an elastic band stretched and fit over the tube; or an adhesive tape wrapped around the tube; or a strip wrapped around the tube and adhered to the tube by an adhesive. An advantage of these types of locator is that the locator can be easily applied to a tube of the urinary drainage system and may also be easily removed from the tube of the urinary drainage system. Thus, the locator can be easily applied to an existing urinary drainage system so that the pinch valve can be used with the existing drainage system and may then be removable for use with a different urinary drainage system.

The locator engaging part may comprise a cylindrical region shaped to receive and engage the band around the tube.

The tube may have a plurality of locators attached thereto for locating the pinch valve on the tube; and the pinch valve may have a plurality of engaging parts for engaging the locators to locate the pinch valve on the tube. For example, there may be two locators and two engaging parts for engaging the two locators.

Providing more than one locator and locating part may ensure that the tube is properly stretched within the valve to be pinched completely when operating the valve. This may be particularly important when the tube being pinched is very soft and otherwise unable to remain straight in the tube receiving region during use. Providing more than one locator may also better prevent rotation or movement of the tube within the tube receiving region.

The present inventor has also realised that the pinching or clamping pressure provided by the pinch valve is an important property of the pinch valve. The pinching pressure needs to be sufficiently high that the tube is pinched sufficiently hard to prevent fluid flow up to a predetermined pressure due to the build-up of urine above the pinching point. However, it is also advantageous to minimise the required pinching pressure, for example to reduce the activation energy of the pinch valve and/or to reduce the power consumption of the actuator and/or to allow for the use of a smaller actuator.

The pinching or clamping pressure may be predetermined to prevent flow of fluid through the valve up to a pressure that is equal to a predetermined height of a column of fluid above the valve, the predetermined height being less than the height of the bladder of the patient above the valve. Thus, the valve may be designed to leak fluid if sufficient fluid builds up above the pinch point of the valve, to prevent refluxing of urine to the kidneys, which would injure the patient.

The present inventor has realised that under normal circumstances the pinching pressure applied by a pinch valve may vary over the lifetime of the pinch valve. This is particularly the case where the actuator of the pinch valve is an electrically powered actuator such as an electric motor, where the output of the electric motor will fluctuate due to effects such as fluctuations in the output of a power source of the electric motor (such as a battery), electromagnetic interference with the electric motor or its power source and dimension tolerances of mechanical components. However, similar variations can occur over the lifetime of a non-electrically powered actuator, such as a manually operated mechanical actuator.

The present inventor has realised that a consistent or uniform clamping force and/or pressure on a specific tube (i.e. a specific diameter of tube) when the pinch valve is closed can be maintained over the operational lifetime of the pinch valve by providing a biasing element between the actuator and the first pinch part that is compressed when the first pinch part compresses the tube against the second pinch part.

Specifically, the biasing element compensates for variations in the output of the actuator, e.g. in the output of an electric motor, by being compressed by a varying degree when the valve is closed. Thus, a consistent clamping force and/or pressure on the tube when the valve is closed can be maintained over the lifetime of the valve, thereby improving the reliability and performance of the valve.

Where the actuator is an electrically powered actuator such as an electric motor, the modulation of the clamping/pinching force provided by the biasing element can prevent the electrically powered actuator from becoming overloaded, for example it can prevent an electric motor from stalling.

Furthermore, the modulation of the clamping force provided by the biasing element can protect the tube which is being pinched between the first and second pinch parts from being damaged when the valve is closed. In particular, clamping the tube too tightly when the valve is closed can damage the tube causing it to split after repeated opening and closing of the valve. This damage to the tube can be prevented by the modulation of the clamping force provided by the biasing element.

Furthermore, in some cases when a tube is clamped too tightly between the first and second pinching parts, there is a risk that the walls of the tube may become stuck/adhered together, thereby preventing the tube from expanding to allow fluid to flow when the valve is reopened. Again, this may be prevented by the modulation of the clamping force provided by the biasing element.

The actuator may be configured to always move to a predetermined position when the valve is closed. For example, where the actuator is an electrical actuator, this may be achieved by the actuator being controlled to operate for a predetermined period of time when closing the valve, so that the actuator is moved to the same position each time the valve is closed. Alternatively, a detector may be provided to detect the position of the actuator and the actuator may be controlled to cease moving the first pinch part when the actuator is moved to a predetermined position. For example, the detector may be a position sensor or a switch. Where the actuator is a manually operated actuator, a stop may be provided to prevent the actuator from being moved beyond a predetermined position. The position of the first pinch part relative to the predetermined position of the actuator is then determined by the extent of compression of the biasing means. This enables the position of the first pinch part and the extent of compression of the biasing element to vary to modulate the clamping force applied to the tube, for example to maintain a consistent clamping force for a specific tube.

Providing a biasing element also enables the pinch valve to be used with tubes of different diameters and/or shapes, because the presence of the biasing element enables the position of the first pinch part to change when the valve is closed to accommodate different diameters and/or shapes of tube in the tube receiving portion. Where the actuator is configured to always move to a predetermined position when the valve is closed, the presence of the biasing element enables the pinch valve to be used with tubes of different diameters and/or shapes without having to change the setting of the actuator travel distance.

Where the pinch-valve is used with different tubes having different shapes and/or sizes, the clamping pressure applied to the tubes by the pinch valve will normally be different. For example, assuming two different diameter tubes with the same wall-thickness, the larger diameter tube will experience a larger clamping force because the biasing element would be compressed to a greater extent than with a smaller diameter tube.

For different tubes having different diameters, the biasing element may cause the clamping force or pressure to be essentially proportional to the diameter of the tube. However, the clamping force also depends on the wall-thickness of the tube. For example, a large diameter tube with a thin wall-thickness will experience a lower clamping force when compared to the same diameter tube with a thick wall-thickness.

As discussed above, the biasing element also prevents the actuator from being overloaded and/or the tube from being damaged by an excessive clamping force when the pinch-valve is used with different tubes having different diameters.

Indeed, providing a biasing element between the actuator and the first pinch part of a pinch valve is an independent improvement of the present invention.

Therefore, according to a second aspect of the present invention there is provided a pinch valve for a urinary drainage system comprising:

a first pinch part and a second pinch part having a tube receiving region therebetween for receiving a tube, wherein the first pinch part is moveable towards the second pinch part for compressing a tube received in the tube receiving region against the second pinch part;

an actuator operable to move the first pinch part; and a biasing element between the actuator and the first pinch part, wherein the biasing element is compressed when the first pinch part compresses a tube against the second pinch part.

The pinch valve according to the second aspect of the present invention may have any one, or, to the extent they are compatible, any combination of the following optional features.

The second aspect of the present invention may be combined with the first aspect of the present invention, optionally with one or more of the optional features of the first or second aspect of the present invention.

The biasing element may be a spring, for example a compression spring, a helical spring, or a wave spring. A wave spring may be particularly advantageous because of its relatively small size.

The first pinch part may be coupled to the actuator by the biasing element.

The biasing element may directly connect the first pinch part to the actuator.

The present inventor has also realised that in some circumstances the actuator may become stuck or become no longer operational, so that the valve may become stuck in the closed state and urine is unable to drain through the valve. For example, this may happen where the actuator is an electrical actuator and where the power supply to the actuator is interrupted, for example because a battery supplying power to the actuator has run out of power. The pinch valve being stuck in the closed position represents a significant risk to the patient, because urine is unable to drain from the urinary bladder. A similar problem may also occur with a manually powered valve, for example where the valve mechanism jams or breaks for some reason.

As discussed above, where the pinch valve is releasably detachable from the tube, in such an emergency situation flow of urine through the tube can be reestablished by detaching the pinch valve from the tube.

However, the present inventor has realised that the safety of the pinch valve can alternatively or additionally be significantly improved by providing an emergency or safety manual release mechanism with which a user can manually move the second pinch part relative to the first pinch part to open the valve.

Therefore, the pinch valve may comprise a release mechanism operable by a user of the pinch valve to move the second pinch part relative to the first pinch part. Thus, the user is able to move the second pinch part to allow urine to drain through the valve even when the actuator is inoperable or broken so that the first pinch part is stuck in the closed position. This may protect the patient from significant harm that could occur if the pinch valve is stuck in the closed position.

Indeed, providing a release mechanism operable by a user to move the second pinch part relative to the first pinch part is an independent improvement of the present invention.

Therefore, according to a third aspect of the present invention there is provided a pinch valve for a urinary drainage system comprising:

a first pinch part and a second pinch part having a tube receiving region therebetween for receiving a tube, wherein the first pinch part is moveable towards the second pinch part for compressing a tube received in the tube receiving region against the second pinch part;

an actuator operable to move the first pinch part; and a release mechanism operable by a user of the pinch valve to move the second pinch part relative to the first pinch part.

The pinch valve according to the third aspect of the present invention may have any one, or, to the extent they are compatible, any combination of the following optional features.

The third aspect of the present invention may be combined with either, or both, of the first or second aspects of the present invention, optionally with one or more of the optional features of the first, second or third aspects of the present invention.

The release mechanism is different, i.e. separate or distinct, from the actuator. Thus, even if the actuator stops working with the valve closed, the release mechanism can be used to move the second pinch part relative to the first pinch part to reopen the valve, thereby preventing injury to the patient.

The release mechanism may move the second pinch part directly away from the first pinch part, i.e. backwards away from the first pinch part, for example in an opposite direction to a direction in which the first pinch part moves when the valve is closed. Alternatively, the release mechanism may move the second pinch part indirectly away from the first pinch part, for example orthogonally (e.g. sideways) or at an angle to the direction in which the first pinch part moves when the valve is closed.

The release mechanism is manually operated, i.e. it operates in response to an action of a user.

In practice the release mechanism will be manually powered instead of electrically powered, i.e. the user will provide the necessary power to cause the release mechanism to move the second pinch part away from the first pinch part.

The release mechanism may comprise a release mechanism actuator on an external surface of the pinch valve; and the release mechanism actuator may be coupled to the second pinch part so that movement of the release mechanism actuator by a user of the pinch valve causes movement of the second pinch part. Thus, a user of the pinch valve is able to move the second pinch part to open the valve when the first pinch part is stuck in the closed position by moving the release mechanism actuator to move the second pinch part.

The release mechanism actuator may be moved forwards and backwards, e.g. into or away from the pinch valve, to move the second pinch part. Alternatively, the release mechanism actuator may be moved along a surface of the pinch valve.

The second pinch part may be provided on an inner surface of a part of a housing of the pinch valve, and the part of the housing may be moveable relative to a remainder of the housing to move the second pinch part. For example the part of the housing may be a panel, flap, sidewall or lid of the housing.

The part of the housing may be detachable from the remainder of the housing, or the part of the housing may be hinged to the remainder of the housing.

The present invention according to any of the first, second or third aspects may have any one, or, to the extent they are compatible, any combination of the following optional features.

The actuator may comprise a valve shuttle, the actuator may be operable to cause linear movement of the valve shuttle, and the first pinch part may be coupled to the valve shuttle so that linear movement of the valve shuttle causes linear movement of the first pinch part. Thus, the first pinch part can be moved to compress the tube by using the actuator to move the valve shuttle.

The actuator may comprise a screw part having an external screw thread, the actuator may be operable to rotate the screw part, the valve shuttle may have an internal screw thread engaged with the external screw thread of the screw part, and the valve shuttle may be prevented from rotating with the screw part, so that rotation of the screw part causes linear movement of the valve shuttle. Thus, the actuator may convert rotational movement, for example of a shaft of a motor or a handle, into linear movement of the first pinch part.

Where the pinch valve comprises the biasing element between the actuator and the first pinch part, the biasing element may couple the first pinch part to the valve shuttle. For example, the biasing element may directly connect the valve shuttle to the first pinch part by being directly connected to each of these parts.

The actuator may be an electrically powered actuator, such as an electric motor.

The pinch valve may comprise an electrical power source for powering the actuator, such as a battery. The battery may be rechargeable. The battery may be replaceable.

The actuator may comprise an electric motor, for example a rotary electric motor having a rotatable drive shaft. An electric motor may have a relatively low power consumption.

Preferably the electrically powered actuator only uses power when moving the first pinch part to open and close the valve, and not when the valve remains in an open or closed state. Thus, the power consumption of the electrically powered actuator will be very low, and the pinch valve can have a small power source (i.e. a small battery) and/or a long lifetime.

The pinch valve may comprise a controller for controlling operation of the actuator, i.e. to control opening or closing of the valve. For example, the controller may be a microcontroller. The controller may be a processor, such as a microprocessor.

The controller may control the actuator to move the first pinch part to open or close the valve. For example, the controller may control the actuator to move the first pinch part to open the valve for a predetermined period of time to drain urine and then control the actuator to move the first pinch part to close the valve after the predetermined period of time. For example, the valve may be opened for approximately 10 minutes.

The controller may control the actuator to operate to move the first pinch part for a predetermined period of time each time the pinch valve is closed, so that the actuator is moved to the same position each time the pinch valve is closed. Alternatively, the pinch valve may comprise a detector, such as a switch or position sensor, that detects when the actuator has moved to a predetermined position, and the controller may be configured to stop operation of the actuator when the detector detects that the actuator has moved to the predetermined position.

The controller may control the actuator in response to an action of a user of the pinch valve, such as a user pressing a button or interacting with some other activation means. In other words, the user is able to manually operate the valve to open or close through the controller.

Alternatively, or in addition, the controller may be configured to automatically control operation of the actuator. Automatic control means the controller controls the operation of the actuator in the absence of any instruction or action of the user. In other words, the controller may control opening and closing of the valve in the absence of any action of the user, for example based on predetermined conditions.

For example, the controller may be configured to cause the actuator to automatically operate (i.e. open or close the valve) at predetermined timings. For example, the controller may automatically cause the actuator to move the first pinch part to open the valve every few hours (e.g. every 2 to 4 hours) for a period of a few minutes (e.g. 10 minutes) to allow the urine to drain into the urine collector, and to then cause the actuator to move the first pinch part to close the valve again.

As mentioned above, periodic opening of the pinch valve to empty the bladder facilitates the filling and re-filling of the bladder. This is believed to help to protect or maintain the bladder's urothelial lining, which provides a natural antibacterial function. Thus, periodic opening of the pinch valve to empty the bladder may help prevent bladder infection. Such periodic opening of the pinch valve can be achieved with a manually operated pinch valve, but can be achieved more efficiently and reliably with an automatically operated pinch valve.

The pinch valve may comprise a manual override for causing the actuator to operate to open the valve at a timing that is not one of the predetermined timings.

The manual override may comprise a manually operable input device, for example a button or switch, that is coupled to the controller so that when a user operates the manually operable input device the controller controls opening and closing of the valve.

The pinch valve may comprise a magnetic switch for causing the actuator to operate, wherein the magnetic switch can be activated by the user bringing a magnet close to the magnetic switch. Thus, the user is able to open the valve manually if needed.

The controller may be configured to also perform other functions, for monitoring a capacity of a battery power source of the pinch valve and controlling the operating parameters of the valve such as the time between openings of the valve and the period of time the valve is open for.

The controller may monitor a capacity of a battery power source of the pinch valve and force the pinch valve to open and remain open when a remaining capacity of the battery power source falls below a threshold value, i.e. when the battery is running low on power. This may prevent the valve from sticking in the closed position if the valve were to run out of battery power while in the closed position.

The controller may be configured to wirelessly communicate with an external device. For example, the controller may be configured to wirelessly send status information about the pinch valve to a wireless control/monitor device. The status information may include information such as the remaining time until the valve next opens when the valve is in the closed state, the time to remain open when the valve is in the open state or under the manual override state, or any operational errors or problems with the pinch valve. The controller may additionally, or alternatively, be configured to receive information from the external device and to save this information into a memory for use by the controller. For example, the external device may be used to communicate with the controller to change parameters of the operation of the pinch valve, such as the predetermined time between openings of the pinch valve or the length of time for which the valve should be opened.

The pinch valve may comprise a first connector for connecting the pinch valve in-line with a first external tube; and a second connector for connecting the pinch valve in-line with a second external tube; and a tube received in the tube receiving region, wherein the tube is in fluid communication with the first and second connectors so that fluid can flow from the first connector to the second connector through the tube.

In other words, in embodiments relating to the second or third aspect of the present invention the pinch valve may be an in-line pinch valve that is connected in the flow-path of the urinary drainage system, instead of a clip-on valve that is arranged around an existing tube of a urinary drainage system.

The pinch valve may comprise: a third connector for connecting a first end of the tube in fluid communication with the first connector; and a fourth connector for connecting a second end of the tube in fluid connection with the second connector.

The third and fourth connectors preferably releasably connect the tube in fluid communication with the first and second connectors. Therefore, the tube can be replaced inside the pinch valve, by disconnecting the tube and reconnecting a new tube, without having to dispose of the entire pinch valve.

BRIEF DESCRIPTION OF THE DRAWINGS

Embodiments of the present invention will now be discussed, by way of example only, with reference to the accompanying Figures, in which.

DETAILED DESCRIPTION OF THE PREFERRED EMBODIMENTS AND FURTHER OPTIONAL FEATURES OF THE INVENTION

Embodiments of the present invention relate to pinch valves for use with a urinary drainage system comprising a urinary catheter for draining urine from a patient's urinary bladder and a urine collection bag for collecting urine drained through the urinary catheter.

A urinary drainage system including the pinch valve of the present invention can be used to control the flow of urine from a patient who requires long-term catheterisation to improve the patient's quality of life.

Figure 1:
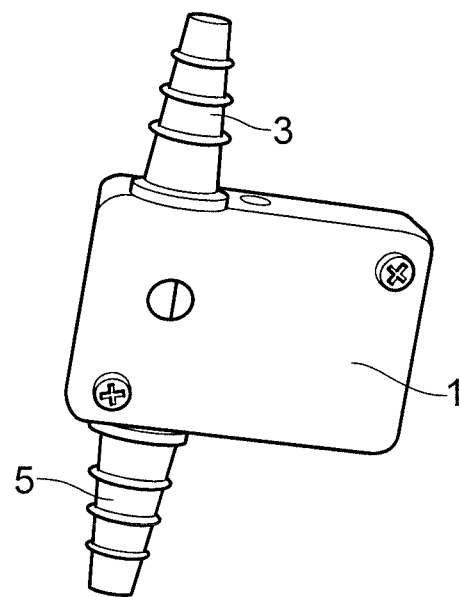
FIG. 1 is an image of the external appearance of a prototype prior art automatic catheter valve.
Figure 2:
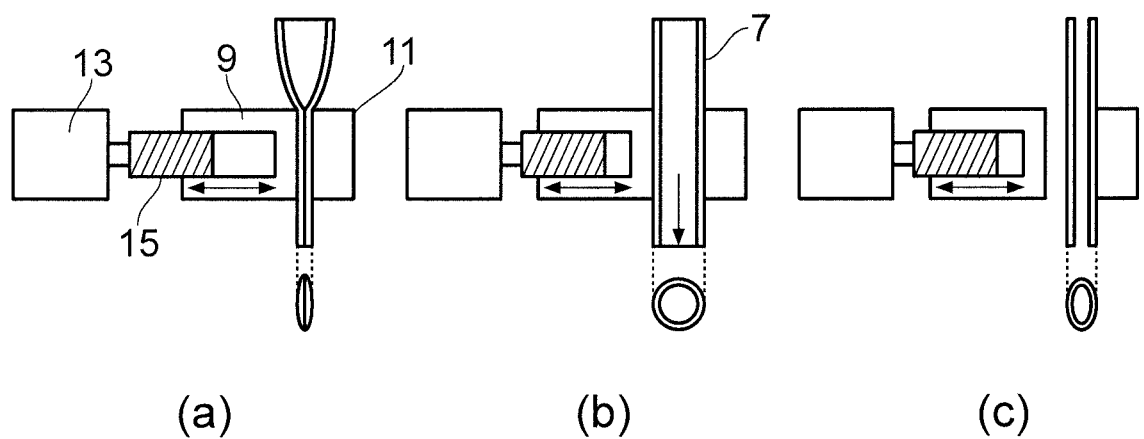
FIGS. 2(a) to 2(c) are schematic illustrations of the internal valve mechanism of the prototype prior art automatic catheter valve shown in FIG. 1.
Figure 3:
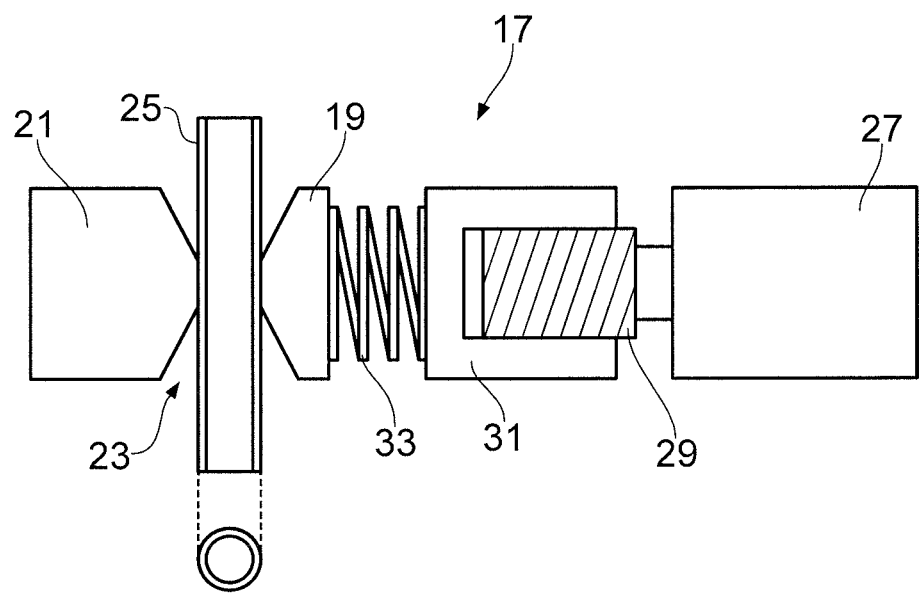
FIG. 3 is a schematic illustration of the internal valve mechanism of a pinch valve according to an embodiment of the present invention.

FIG. 3 is a schematic illustration of the internal valve mechanism of a pinch valve according to an embodiment of the present invention.

As shown in FIG. 3, the pinch valve 17 comprises a first pinch part 19 and a second pinch part 21 separated by a tube receiving region 23 for receiving a tube 25. The first pinch part 19 and second pinch part 21 are arranged on opposite sides of the tube receiving region 23, for pinching the tube 25 received in the tube receiving region 23 therebetween.

In normal operation of the pinch valve 17, the second pinch part 21 does not move relative to the pinch valve 17. Therefore, the second pinch part 21 can be considered to be a stop part against which the tube 25 is compressed (pinched) by the first pinch part 19.

As described below, the first pinch part 19 is moveable linearly towards and away from the second pinch part 21 by an actuator. Specifically, in order to close the pinch valve 17 so that fluid is prevented from flowing through the tube 25, the first pinch part 19 is moved towards the second pinch part 21 to compress the tube 25 therebetween. In order to open the pinch valve 17 so that fluid can flow through the tube 25, the first pinch part 19 is moved away from the second pinch part 21.

The first pinch part 19 can be considered to be a piston for compressing the tube 25 against the second stop part 21.

The actuator for moving the first pinch part 19 relative to the second pinch part 21 comprises a rotary electric motor 27, an externally threaded lead screw 29 and a valve shuttle 31.

The externally threaded lead screw 29 is connected to a rotary shaft of the electric motor 27 so that the externally threaded lead screw 29 rotates with the rotary shaft. The valve shuttle 31 has an internal bore in which the externally threaded lead screw 29 is received. The internal bore has a screw thread which is threadably engaged with the external screw thread of the externally threaded lead screw 29. The valve shuttle 31 is prevented from rotating with the externally threaded lead screw 29. Therefore, rotation of the externally threaded lead screw 29 causes linear movement of the valve shuttle 31, the direction of the linear movement depending on the direction of rotation of the externally threaded lead screw 29.

The first pinch part 19 is directly connected to the valve shuttle 31 by a compression spring 33. Therefore, linear displacement of the valve shuttle 31 is transmitted to the first pinch part 19 to cause linear displacement of the first pinch part 19 through the compression spring 33.

A battery (not illustrated) may also be present in the valve 17 to provide electrical power to the electric motor 27.

The electric motor 27 only uses power when moving the valve shuttle 31 to open or close the valve, and not when the valve remains in an open or closed state. Therefore the electric motor, 27 has a very low power consumption.

FIG. 3 shows the pinch valve 17 in an open state, in which the valve shuttle 31 has been retracted away from the second pinch part 21 as far as possible by operation of the electric motor 27. In this configuration, the first pinch part 19 is retracted away from the second pinch part 21 as far as possible so that the tube 25 is not compressed (or not significantly compressed) between the first pinch part 19 and the second pinch part 21. In this configuration no (or no significant) force is applied to the first pinch part 19, and therefore the compression spring 33 is not (or not significantly) loaded or compressed. In this configuration fluid is able to flow through the tube 25 through the valve 17, because the tube 25 is not (or not significantly) compressed.

Figure 4:
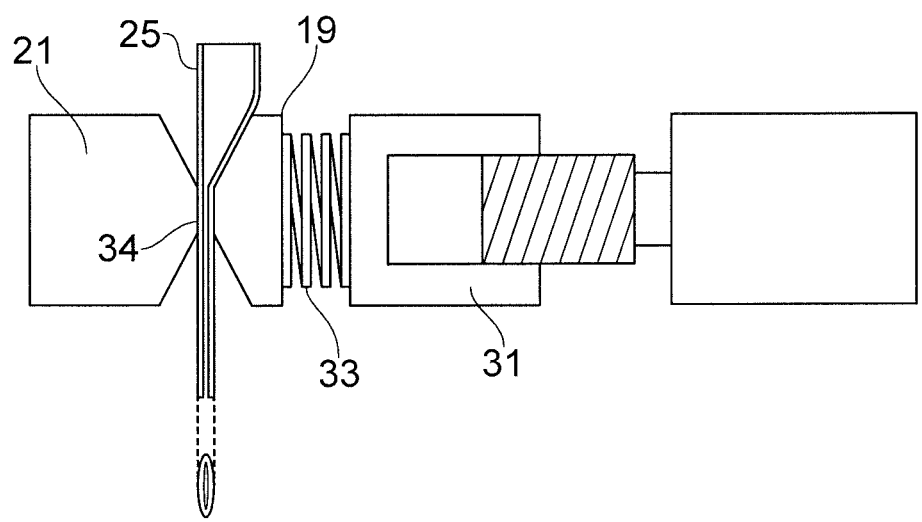
FIG. 4 is a schematic illustration of the internal valve mechanism of a pinch valve according to an embodiment of the present invention.

FIG. 4 shows the pinch valve after the electric motor 27 has been operated to linearly displace the valve shuttle 31 towards the second pinch part 21, so that the tube 25 is compressed (pinched) at a pinch point 34 between the first pinch part 19 and the second pinch part 21. This corresponds to a closed state of the valve 17. In particular, fluid is prevented from flowing through the tube 25 through the valve 17 because the tube 25 is pinched closed at the pinch point 34. In this configuration the plunger 19 has a force applied to it and the compression spring 33 is loaded and compressed.

As discussed below, the tube 25 may be an existing (external to the valve 17) tube of the urinary drainage system that has been received in the tube receiving region 24 by the valve being clipped on to, positioned or arranged around, attached or connected to the tube.

Alternatively, in some embodiments the valve may be an inline valve that is connected inline between a urinary catheter and urine collection bag of the urinary drainage system. Specifically, the valve may have input and output connectors for connecting the valve inline between a urinary catheter and urine collection bag of the urinary drainage system, and the tube 25 may be an internal tube of the valve that extends between the input and output connectors to provide a flow path for fluid in the valve between the input and output connectors. In this case, the tube 25 may be a very thin-walled tube, for example having a wall thickness of 50-100 μm.

The compression spring 33 ensures that the clamping force and/or pressure applied to the tube 25 when the valve 17 is in the closed state is consistent throughout the operational lifetime of the valve 17 (for a given diameter of tube), regardless of small fluctuations in the output of the electric motor 27 caused, for example, by fluctuations in the output of a battery power supply, electromagnetic interference, or by dimension tolerances of mechanical components or of the tube 25.

The compression spring 33 also enables the valve 17 to adapt to small variations in the shape or size (diameter) of the tube 25 received in the tube receiving region, because it enables the position of the first pinch part to vary when the valve is closed depending on the extent of compression of the compression spring 33. The pinch valve can therefore be used with tubes having different diameters.

The electric motor actuator used in this embodiment results in a significant reduction in power consumption, and therefore significantly improved efficiency, relative to other possible actuators such as a solenoid valve actuator.

As discussed above, the valve 17 preferable includes a battery to supply power to the electric motor 27. Thus, the valve is standalone and fully portable.

Figure 5:
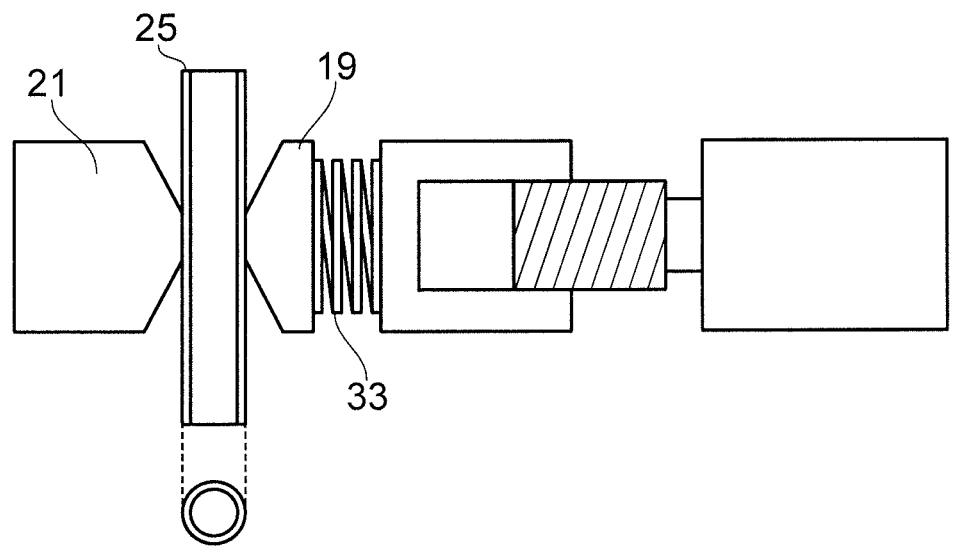
FIG. 5 is a schematic illustration of the internal valve mechanism of a pinch valve according to an embodiment of the present invention.

FIG. 5 shows the pinch valve in an emergency open state. In this state the first pinch part 19 is in the same position as in the open state of FIG. 4. In other words, the first pinch part 19 has been moved as far as possible towards the second pinch part 21 to compress the tube 25 therebetween. However, a manual release mechanism (not shown) has been used to move the second pinch part 21 away from the first pinch part 19 to release at least some of the pressure on the tube 25, so that the tube 25 is no longer fully compressed between the first pinch part 19 and second pinch part 21 and fluid is able to pass through the tube 25 through the valve 17.

If the second pinch part 21 is moved sufficiently far away from the first pinch part 19, the compression spring 33 may no longer be loaded and the first pinch part 19 may not apply any force to the tube 25. If the second pinch part is moved less than this, the pressure from the urine above the pinch point 34 may be sufficient to overcome the reduced pressure applied by the first pinch part 19 and to allow the tube 25 to expand sufficiently by compressing the compression spring 33 to allow some fluid to flow.

The emergency open state is particularly useful where the first pinch part 19 is no longer moveable for some reason, so that the valve 17 would otherwise be stuck in the closed position and urine would continue to build up above the pinch point 34. This may occur, for example, where the power supply to the electric motor 27 is interrupted, for example because a battery power supply is exhausted.

The manual release mechanism may comprise an actuator that is attached to the second pinch part 21 and moveable by a user of the valve to move the second pinch part 21. For example, the second pinch part 21 may be provided on the inner side of a part of a housing of the valve that is removable from the housing or hinged to the housing so that the second pinch part 21 can be moved by moving the part of the housing. Alternatively, there may be a protrusion connected to the second pinch part 21 that is slidably movable within a slot in a housing of the valve to slidably move the second pinch part 21.

Although FIG. 5 shows both the compression spring and the release mechanism, the valve may only have one of these features. Thus, the valve may have the release mechanism without the compression spring, or the compression spring without the release mechanism.

In some embodiments of the present invention the catheter valve is an automatic catheter valve wherein operation (i.e. opening and closing) of the valve occurs automatically with no input from the user/patient, for example based on a predetermined condition(s).

This is achieved in some embodiments of the present invention by the valve having a controller, for example a microcontroller or processor/microprocessor, for controlling the operation of the electric motor.

The controller may be preprogrammed to control the opening and closing of the valve based on predetermined timings. For example, the controller may be preprogrammed to control the valve to open to allow urine to drain through the valve at predetermined intervals, for example every few hours (e.g. every four hours), or at predetermined absolute times. The controller may be configured to keep the valve open for a predetermined period of time each time it is opened, for example 10 minutes, to allow sufficient urine to drain through the valve and to then close the valve again until the next time it is opened.

Opening the valve periodically in this manner is expected to have a number of advantages. Firstly, filling and emptying the bladder at regular intervals, for example 6 to 10 times in 24 hours, has an effect of washing out bacteria and encrustation in the bladder and catheter tube, which is an important defence against infection of the bladder. Furthermore, allowing the bladder to become full and stretched periodically is advantageous in maintaining the health and function of the bladder.

Automatic control of the opening and closing of the valve is advantageous because it does not rely on the operation of a user. For example, a patient may forget to periodically open the valve themselves, leading to subsequent health problems. In addition, a patient may not have sufficient manual dexterity to operate a manually activatable valve.

Where the valve is an automatic valve, a manual override may also be provided to enable the user to cause the valve to open at time other than the predetermined times controlled by the controller. For example, there may be a switch or button that a user can press to cause the valve to open for a period of time (for example 10 minutes) before closing again. Alternatively, a non-contact manual override may be provided to allow a user with limited manual dexterity to cause the valve to open for a period of time. For example, the valve may comprise a magnetic reed switch for triggering the valve to open for a period of time (e.g. via the controller) and a user may trigger the magnetic reed switch by bringing a magnet into close proximity with the magnetic reed switch. Alternatively, the operation of the valve may be controllable by a remote control or other device in wireless communication with the valve. For example, the controller of the valve may be configured to wirelessly communicate with an external device that can be used to instruct the controller to cause the valve to open for a period of time.

Such a manual override may also be usable to extend the period of time for which the valve is open when the valve is in the open state.

As mentioned above, in some embodiments the controller may be configured to wirelessly communicate with an external device. For example, in some embodiments the controller may be configured to send status information about the valve to an external wireless monitor, for example information relating to whether the valve is open or closed, and how long it will remain in its current state for. The controller may also inform the wireless monitor if there are any problems or errors with the operation of the valve. The wireless monitor may have a display for displaying information about the valve to a patient or other user.

The controller may also be configured to monitor a status of a battery of the valve for supplying electrical power to the electrical motor 27, for example using a battery monitor. The controller may be configured to force the valve to open and to stay open where the remaining power of the battery falls below a predetermined threshold. This may prevent the valve from running out of battery in the closed state and becoming stuck in the closed state, which would be a significant safety risk.

Figure 6:
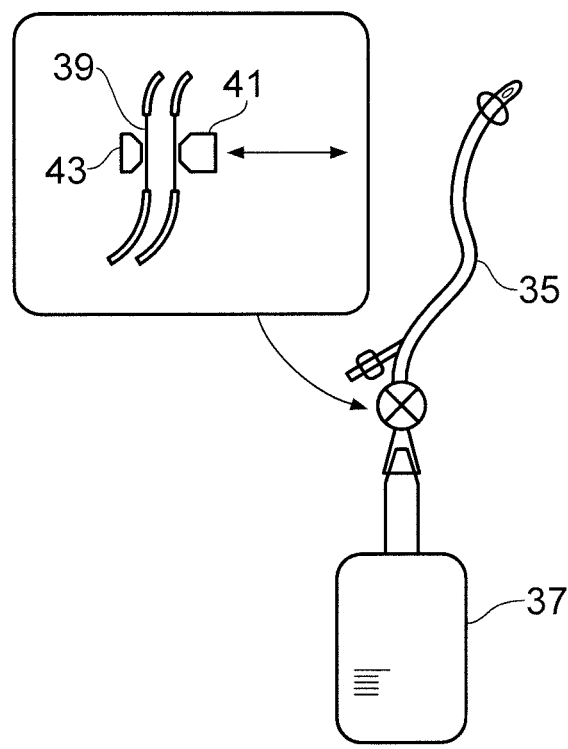
FIG. 6 is a schematic illustration of a urinary drainage system according to an embodiment of the present invention.
Figure 7:
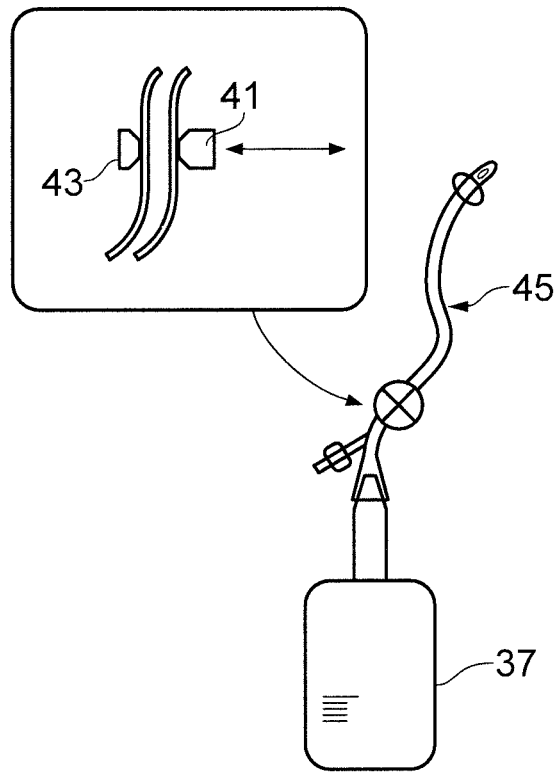
FIG. 7 is a schematic illustration of a urinary drainage system according to an embodiment of the present invention.
Figure 8:
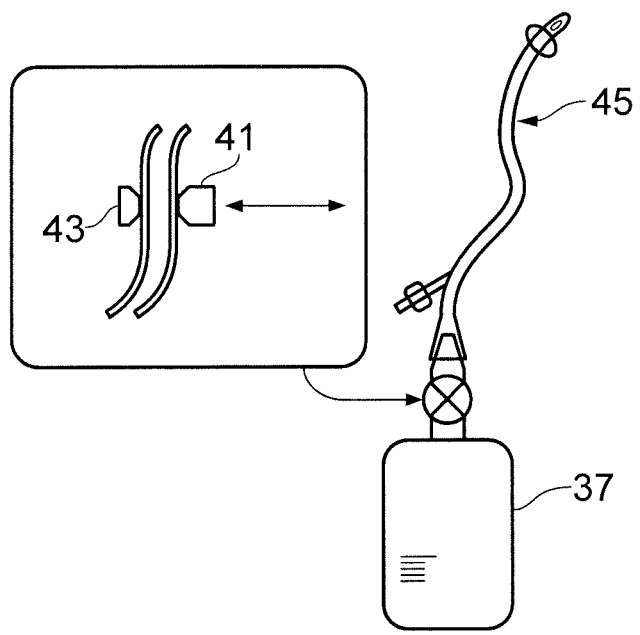
FIG. 8 is a schematic illustration of a urinary drainage system according to an embodiment of the present invention.

FIGS. 6 to 8 relate to different ways in which pinch valves according to embodiments of the present invention can be used with urinary drainage systems.

FIG. 6 shows a pinch valve according to an embodiment of the present invention being used with a urinary drainage system comprising a specially designed Foley urinary catheter 35 and a urine collection bag 37 connected to an output end of the urinary catheter 35 by a cone connector.

As shown in the enlarged portion in FIG. 6, shown inside the box, the urinary catheter 35 has a section of its length 39 over which the wall-thickness of the catheter 35 is reduced. The pinch valve is positioned around this section of the catheter 35 with this section 39 of the catheter 35 received in the tube receiving portion of the pinch valve, so that this section 39 is positioned between the first and second pinch parts 41, 43. For simplicity, only the first and second pinch parts 41, 43 of the valve are shown in FIG. 6.

This arrangement is advantageous because the pinch valve is closed by pinching the thin-walled portion, which is less strong/stiff than the remainder of the tube of the catheter 35. Thus, less force is required from the pinch valve to compress the tube, and therefore the activation energy and power consumption of the pinch valve are reduced.

The pinch valve may be a pinch valve as described above.

The thin-walled section may have a wall thickness of between 50-100 μm.

As discussed above, since the pinch valve is positioned around the catheter 35, no part of the pinch valve comes into contact with the urine flow and no additional connectors to the catheter 35 are required. Thus, the bio-isolation of the urinary drainage system is maintained and the risk of encrustation occurring in the urinary drainage system is not increased.

FIG. 7 shows the pinch valve arranged around (and attached to) a standard Foley urinary catheter 45 of a urinary drainage system, i.e. without the thin-walled portion. The other features of this embodiment are the same as the embodiment illustrated in FIG. 6. An advantage of this arrangement is that it is not necessary to use a specially designed catheter in the urinary drainage system. Therefore, the valve can be applied to existing urinary catheters 45 in existing urinary drainage systems.

FIG. 8 shows the same urinary drainage system as in FIG. 7 but in this embodiment the pinch valve is positioned around an input tube of the urine collection bag 37, instead of around part of the urinary catheter 45. As above, an advantage of this arrangement is that the pinch valve can be used with existing urinary drainage systems, because it does not require a specially designed catheter or urine collector.

Of course, in another embodiment the input tube of the urine collection bag may have a thin-walled section for being received in the tube receiving region of the pinch valve, similar to that shown in FIG. 6.

In any of these embodiments, the pinch valve may be positioned around the tube of the catheter or urine collection bag while the urine drainage system is in situ in a patient draining urine from the patient's bladder, for example where the catheter is an indwelling catheter inserted into a patient's bladder.

FIGS. 9 to 14 disclose example mechanisms by which the pinch valve can be attached to an existing tube of a urinary drainage system, for example as illustrated in FIGS. 6 to 8.

Since these FIGS. relate primarily to mechanisms by which the pinch valve can be attached to an existing tube of a urinary drainage system, the pinching mechanism of the pinch valve is not shown or described in any detail. It is to be understood that the pinch valve mechanism may be any one of the pinch valve mechanisms described above or illustrated in FIGS. 2 to 5.

Figure 9:
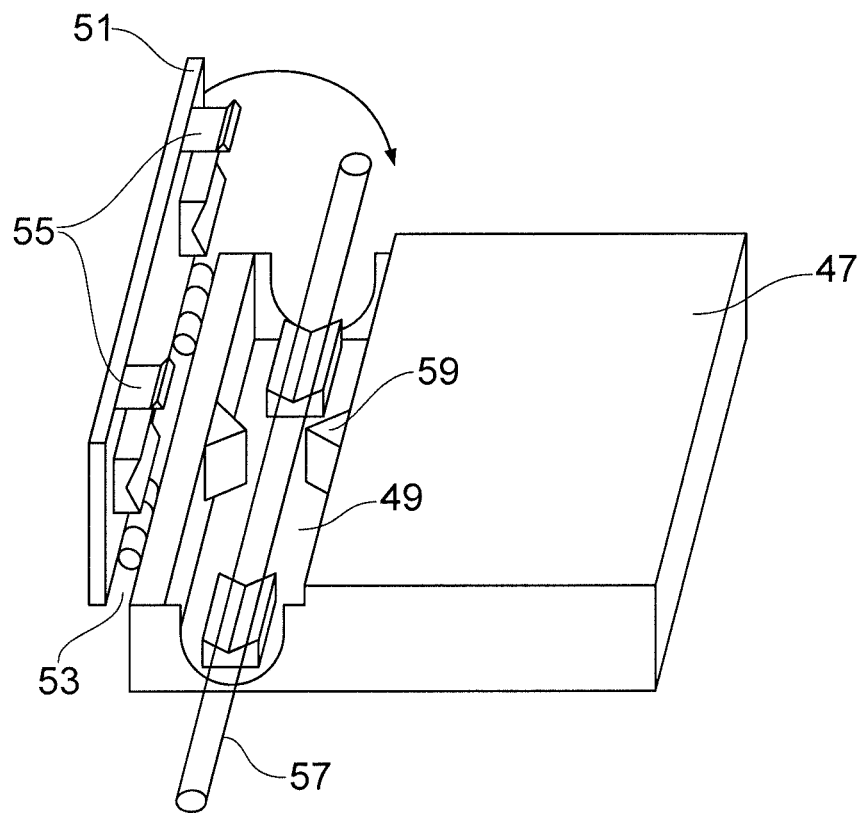
FIG. 9 is a schematic illustration of a mechanism for attaching a pinch valve to a tube or a urinary drainage system according to an embodiment of the present invention.

FIG. 9 shows a mechanism for attaching a pinch valve to an existing tube of a urinary drainage system. As shown in FIG. 9, the pinch valve has a main housing 47 having an elongate channel 49 for receiving a tube of a urinary drainage system that extends between openings on opposite side surfaces of the main housing 49.

The pinch valve comprises a hinged flap 51 (or lid) that is hinged to the main housing 49 by hinges 53 and that can be rotated around the hinges 53 to cover or uncover the elongate channel 49. When the hinged flap 51 covers the elongate channel 53 it is flush with a main surface of the main housing 49.

The hinged flap 51 has latches 55 attached thereto for latching the hinged flap 51 in place when the hinged flap 51 covers the elongate channel 49. The holding force of the latches 55 can be overcome by a user of the pinch valve to move the hinged flap 51 to uncover the elongate channel 49 when necessary.

As shown in FIG. 9, a tube 57 of the urinary drainage system, for example a tube of a catheter or urine drainage bag, can be received in the elongate channel 49 by the hinged flap 51 being rotated around the hinges 53 to uncover the elongate channel 49. The tube 57 can then be moved sideways into the elongate channel 49 so that it is received in the elongate channel 49 between the pinch mechanism 59 of the pinch valve. The hinged flap 51 can then be rotated back around the hinges 53 to cover the elongate channel 49 so that the tube 57 is rotated in the elongate channel 49. The hinged flap is held in this position by the latches 55. Thus, the pinch valve can be attached to the tube of the urinary drainage system.

Thus, the pinch valve can easily be positioned around and attached to a tube of a urinary drainage system even while the urinary drainage system is in situ on a patient.

As mentioned above, it can be advantageous to restrict movement of the tube 57 within the elongate channel 49, for example to ensure that the tube 57 remains correctly positioned between the first and second pinch parts of the pinch mechanism 59, so that the pinch mechanism correctly pinches the tube 57 when the valve is closed.

Figure 10:
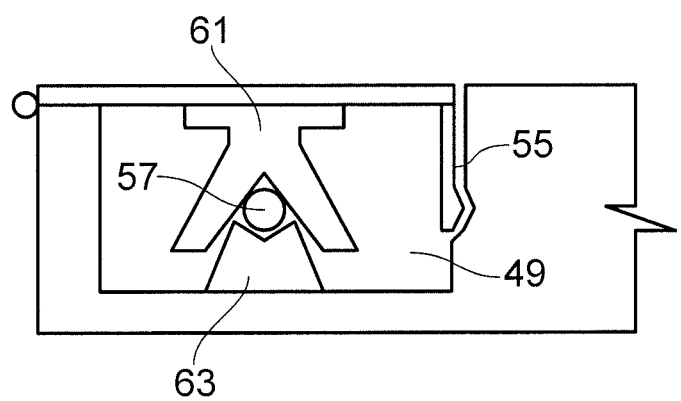
FIG. 10 is a schematic illustration of a mechanism for attaching a pinch valve to a tube or a urinary drainage system according to an embodiment of the present invention.
Figure 11:
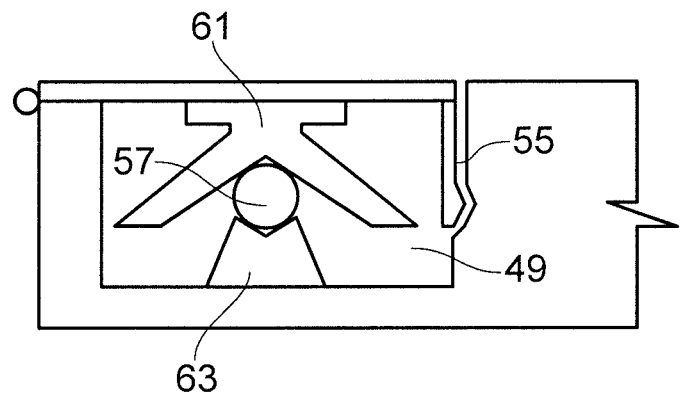
FIG. 11 is a schematic illustration of a mechanism for attaching a pinch valve to a tube or a urinary drainage system according to an embodiment of the present invention.

FIGS. 10 and 11 show a first example of how the tube can be correctly positioned and/or held in position in the elongate channel 49. The other features of the pinch valve may as be as shown in FIG. 9 and are not described.

As shown in FIGS. 10 and 11, in the first example the pinch valve comprises first 61 and second 63 gripping parts (or clamping parts) for gripping a tube 57 received in the elongate channel 49 therebetween.

In this embodiment, each of the gripping parts 61, 63 has a V-shaped portion for abutting the tube 57. Each of the gripping parts 61, 63 is made of a non-slip material such as silicone, so that there is high friction between the gripping parts 61, 63 and the tube 57.

As shown in FIG. 10, the first gripping part 61 is fixed on an inner side of the hinged flap 51 and the second gripping part 61 is fixed on an inner surface of the housing on an opposite side of the elongate channel 49. Thus, when the hinged flap 51 is moved to cover the elongate channel 49 the first 61 and second 63 gripping parts are opposed to each other and grip a tube 57 received in the elongate channel 49 therebetween, as shown in FIG. 10.

One or both of the gripping parts 61, 63 is flexible or resiliently deformable, so that the gripping part is able to deform. In this embodiment, the first gripping part 61 is more deformable (softer or more flexible) than the second gripping part. Thus, the first gripping part 61 is able to deform around a tube 57 received in the elongate channel 49 to better hold the tube 57 in position in the elongate channel 49.

Furthermore, as shown in FIG. 10, the deformable nature of the first gripping part 61 enables the gripping part to grip tubes of different diameters received in the elongate channel 49. FIG. 10 shows a tube 57 having a greater diameter than the tube 57 in FIG. 9. The first gripping part 61 has been more deformed in FIG. 10 than in FIG. 9 by the side walls of the V-shaped portion being splayed further apart to accommodate the larger diameter. Thus, the gripping parts 61, 63 are able to accommodate tubes having different diameters while still ensuring that the tube are properly held and/or positioned within the elongate channel 49.

The gripping of the tube 57 may prevent movement of the tube 57 within the elongate channel 49, for example sliding movement of the tube 57 along the channel 49.

Figure 12:
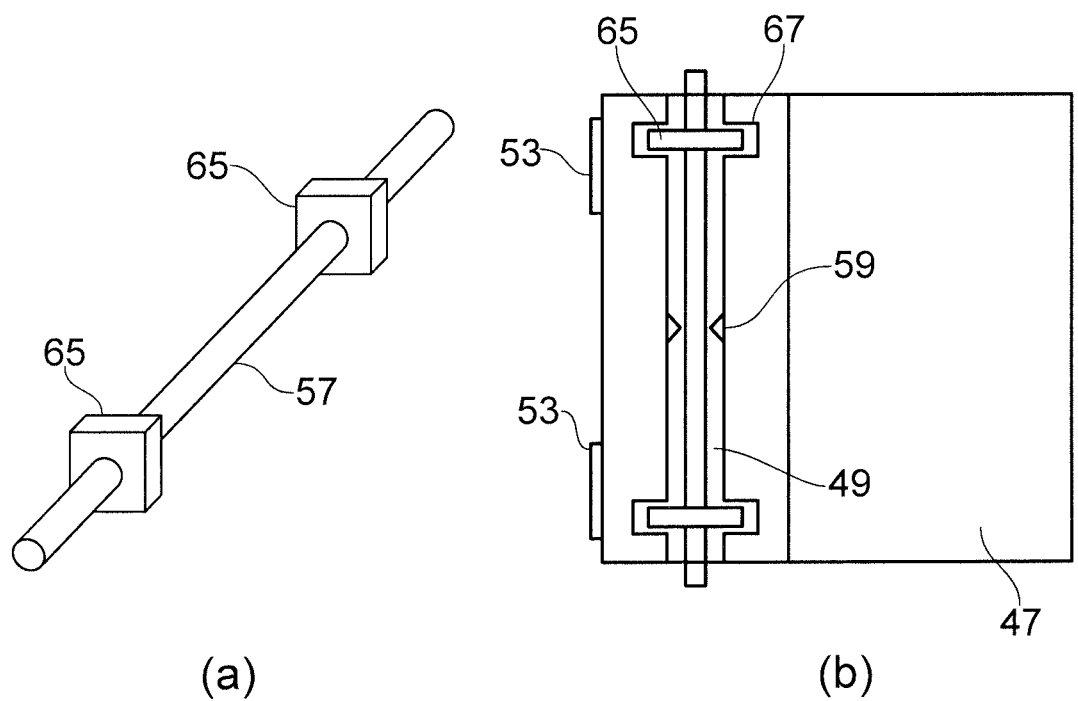
FIGS. 12(a) and 12(b) are schematic illustrations of a mechanism for attaching a pinch valve to a tube of a urinary drainage system according to an embodiment of the present invention.

FIG. 12 shows a second example of how the tube can be correctly positioned and/or held in the elongate channel 49. This example may be used as an alternative to, or in addition to, the first example. The other features of the pinch valve may as be as shown in FIG. 9.

As shown in FIG. 12(a), in this example the tube 57 of the urinary drainage system, for example a tube of a urinary catheter, has two shaped locators 65 positioned along its length. The shaped locators 65 may be integral with the tube 57, for example moulded with the tube 57, or may be attached to the tube 57, for example by an adhesive or by welding.

The pinch valve has two locator engaging compartments 67 positioned along the elongate channel 49. The size and shape of the locator engaging compartments 67 corresponds to the size and shape of the shaped locators 65, so that the shaped locators 65 can be received inside the locator engaging compartments 67. The spacing between the locator engaging compartments 67 is the same as the spacing between the shaped locators 65 on the tube 57.

Thus, as shown in FIG. 12(b), the tube 57 can be received in the elongate channel 47 with the shaped locators 65 received in the locator engaging compartments 67.

The engagement between the shaped locators 65 and the locator engaging compartments 67 allows the pinch valve to be precisely located on the tube, for example so that a thin-walled section of the tube is received in the elongate channel 49 between the pinching mechanism 59. In addition, this engagement allows control of the specific orientation between the pinch valve and the tube. Furthermore, the use of two shaped locators 65 and locator engaging compartments 67 ensures that the tube is properly stretched within the elongate channel 49 so that it can be correctly pinched by the pinching mechanism when the valve is closed. This is particular important when the valve being pinched is soft and therefore unable to remain straight in the elongate channel 49 during operation.

The engagement between the shaped locators 65 and the locator engaging compartments 67 may also prevent movement of the tube 57 within the elongate channel 49, for example sliding movement of the tube 57 along the channel 49.

Figure 13:
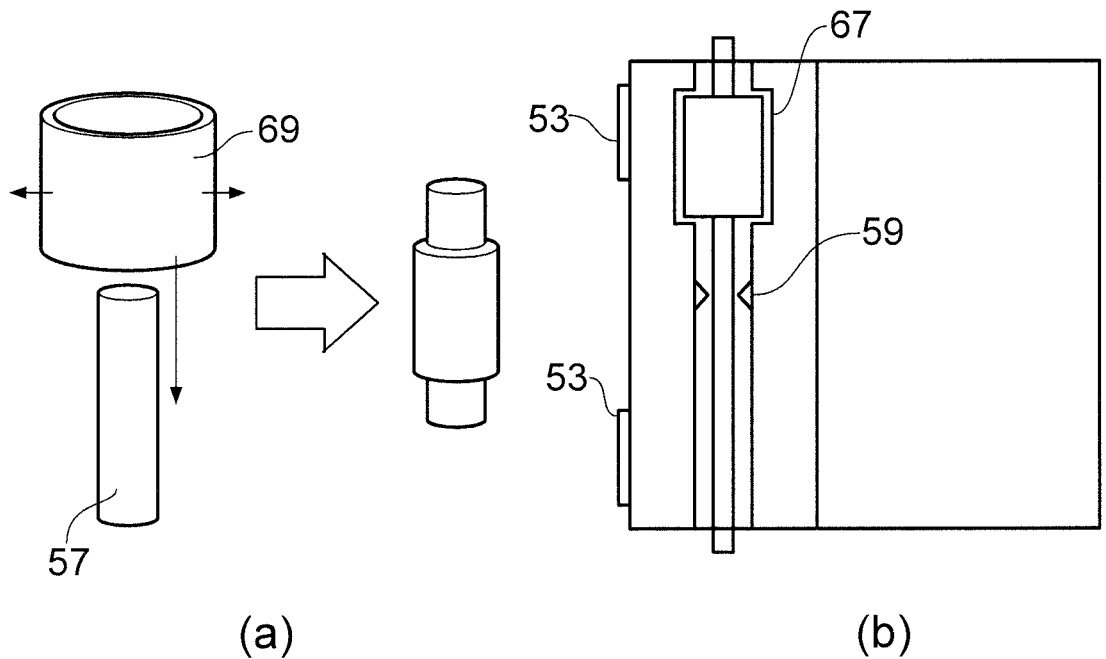
FIGS. 13(a) and 13(b) are schematic illustrations of a mechanism for attaching a pinch valve to a tube of a urinary drainage system according to an embodiment of the present invention.

FIG. 13 shows a third example of how the tube can be correctly positioned and/or held in the elongate channel 49. This example may be used as an alternative to, or in addition to, the first example. The other features of the pinch valve may as be as shown in FIG. 9.

In this embodiment a resilient band 69 (e.g. an elastic band) is stretched and fitted around the tube 57, as shown in FIG. 13(a). Once the resilient band 69 has been fitted around the tube 57, the resilient band 69 functions as a shaped locator as in the example of FIG. 12. Thus, as in the second example, when the tube 57 is received in the elongate channel 49 the resilient band is received in a locator engaging compartment 67 of the pinch valve. Again, this acts to precisely locate the tube 57 in the elongate channel 49 and to prevent movement of the tube 57 within the elongate channel 49.

An advantage of this embodiment is that the resilient band 69 can easily be fitted to an existing tube of a urinary drainage system, meaning the present invention can easily be retro-fitted to existing urinary drainage systems.

Furthermore, an advantage of using a resilient band 69 as in this embodiment is that the same resilient band 69 can be used with different tubes having different diameters. Thus, the present invention can easily be used with tubes of different diameters.

Figure 14:
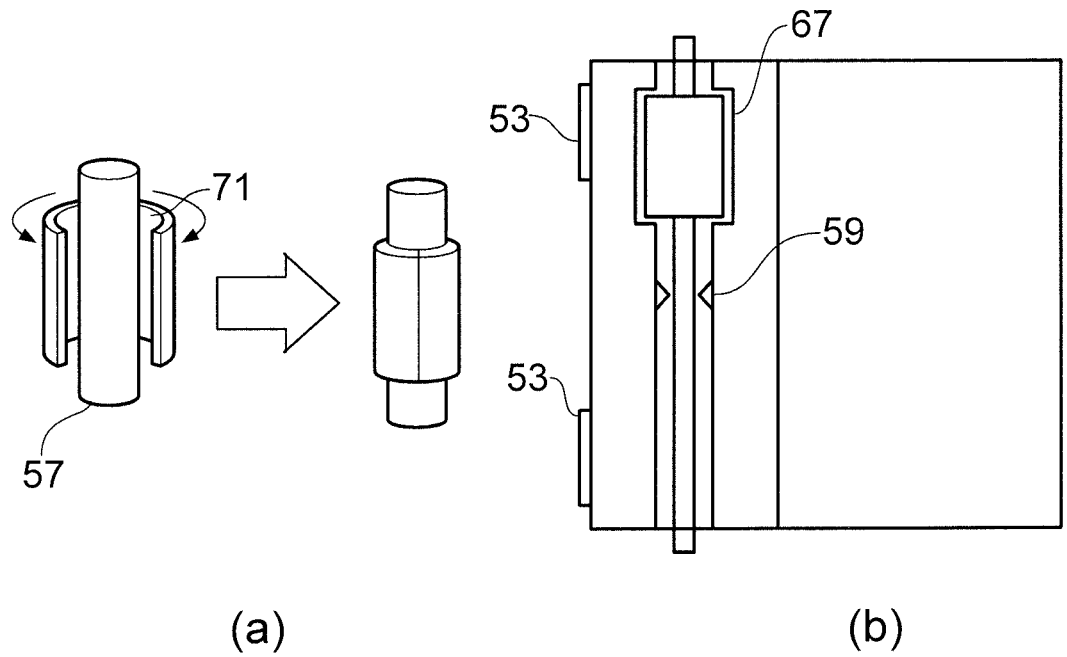
FIGS. 14(a) and 14(b) are schematic illustrations of a mechanism for attaching a pinch valve to a tube of a urinary drainage system according to an embodiment of the present invention.

FIG. 14 shows a fourth example of how the tube can be correctly positioned and/or held in the elongate channel 49. This example may be used as an alternative to, or in addition to, the first example. The other features of the pinch valve may as be as shown in FIG. 9.

The fourth example differs from the third example shown in FIG. 13 in that an adhesive tape 71 is wrapped around the tube 57 to form the shaped locator. Otherwise, the other features of this example are the same as in the third example.

The adhesive tape 71 may comprise a strip of material having an adhesive material on one side thereof for sticking the strip of material to the tube. Thus, the adhesive tape 71 can be wrapped around the tube with the layer of adhesive material against the tube to stick the adhesive tape to the tube.

As with the third example, when the tube 57 is received in the elongate channel 49 the adhesive tape 71 forming a shaped locator is received in the locator engaging compartment 67 of the pinch valve, thereby correctly locating the pinch valve on the tube and preventing movement of the tube in the elongate channel 49.

As with the third example, an advantage of this embodiment is that the adhesive tape 71 can be applied to any existing tube, meaning that the present invention can be used with any existing urinary drainage system.

An appropriate length of adhesive tape 71 can be cut by a user from a larger roll of the adhesive tap 71 for application to the tube 57. Therefore, this example can easily be used with different tubes having different diameters by the user cutting a length of the adhesive tape 71 that is appropriate to the diameter of the tube in question (i.e. that is sufficient to encircle the tube).

One example mechanism for moving the second pinch part relative to the first pinch part to open the valve, for example in an emergency situation such as where the first pinch part has become stuck in the closed position, was discussed above with reference to FIG. 5. Further examples will now be discussed with reference to FIGS. 15 and 16.

The actuator mechanism of the pinch valve shown in the embodiment of FIG. 15 is the same as the actuator mechanism discussed above in relation to the preceding FIGS. and is not described here again for conciseness.

Figure 15A:
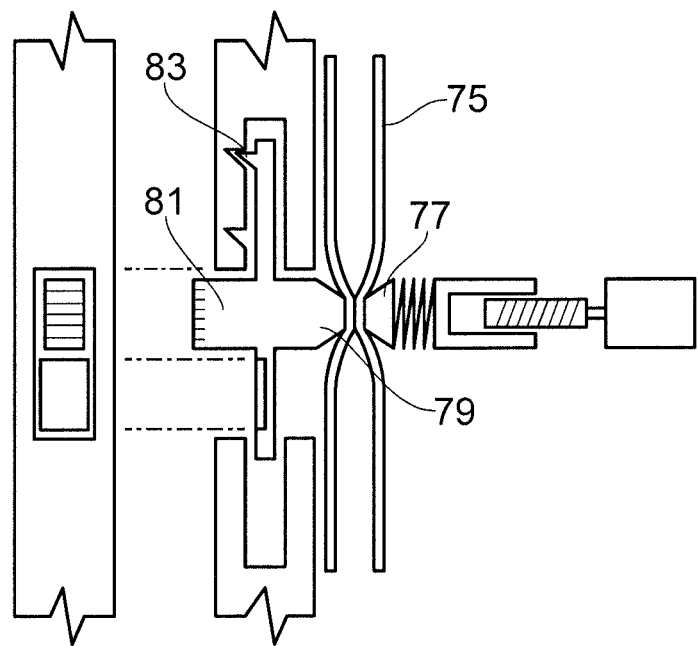
FIGS. 15(a) and (b) are schematic illustrations of a pinch valve having an emergency release mechanism according to an embodiment of the present invention.

FIG. 15(a) shows the pinch valve in the closed state in which the tube 75 is compressed between the first pinch part 77 (which is moved by the actuator) and the second pinch part 79.

The pinch valve according to this embodiment has a fail-safe mechanism for moving the second pinch part 79 relative to the first pinch part 77 to open the valve if the first pinch part 77 becomes stuck in the closed position, for example where the power supply to the electric motor is interrupted while the pinch valve is closed. This will enable fluid flow through the valve to be re-established even when the valve has failed in the closed position.

Specifically, as shown in FIG. 15, the second pinch part 79 is a slider that is slidably movable along the housing of the pinch valve between a first position and a second position. In the first position shown in FIG. 15(a), the second pinch part 79 is immediately opposite the first part 77 so that the tube 75 is compressed therebetween, so that no fluid can flow. This corresponds to the normal closed state of the pinch valve.

Figure 15B:
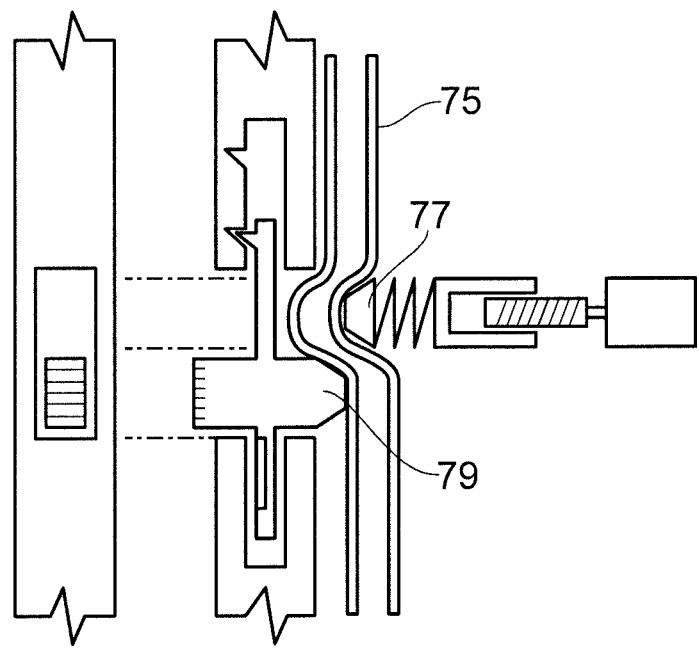

When the second pinch part 79 is slid along the housing to the second position shown in FIG. 15(b), the second pinch part 79 is no longer immediately opposite the first pinch part 77 so that the tube 75 is no longer compressed therebetween. Instead, the tube 75 is able to move into the space previously occupied by the second pinch part 79 opposite the first pinch part 77 so that it is not compressed any more, or not compressed by the same amount, so that fluid can flow through the valve.

As shown in FIG. 15, part of the second pinch part 79 protrudes from the housing of the pinch valve to the outside thereof where it acts as an actuator 81 that a user of the pinch valve can use to slide the second pinch part 79 along the housing.

In order to prevent the fail-safe mechanism from being used accidentally, a latch may be provided to prevent the second pinch part 79 from sliding along the housing while the latch is engaged. In the embodiment of FIG. 15, the latch is a uni-direction latch 83 which can be disengaged by pressing the second pinch part 79 towards the first pinch part 77, so that the second pinch part 79 can be slid along the housing. In normal use, when the valve is closed the pressure on the second pinch part 79 will keep the latch 83 engaged so that the second pinch part 79 cannot be moved without the user first pressing it in to disengage the latch 83.

The latch 83 may engage in both the first and second positions of the second pinch part 79, so that the failsafe mechanism cannot be accidentally opened or closed. This should ensure that once the failsafe is engaged, it will not accidentally return to normal operation mode. This may be achieved for providing first and second engagement portions for engaging the latch 83 to prevent movement of the second pinch part 79 when the second pinch part 79 is in the first or second position.

As shown in FIG. 15, there may also be a visual indicator, for example green and red coloured regions, to show when the fail-safe is open or closed.

Another example of a fail-safe mechanism for moving the second pinch part relative to the first pinch part is shown in FIG. 16.

The actuator mechanism of the pinch valve shown in the embodiment of FIG. 16 is the same as the actuator mechanism discussed above in relation to the preceding FIGS. and is not described here again for conciseness.

Figure 16A:
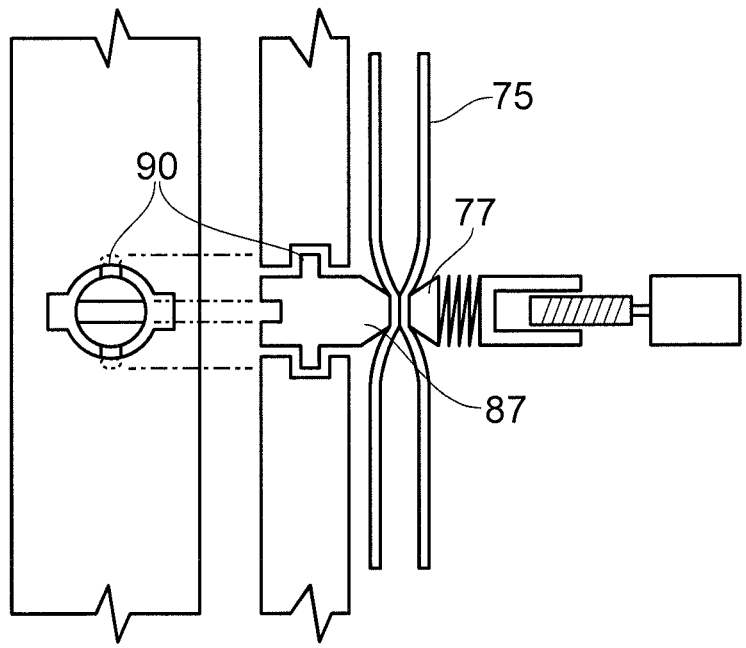
FIGS. 16(a) and (b) is a schematic illustration of a pinch valve having an emergency release mechanism according to an embodiment of the present invention.

FIG. 16(a) shows the pinch valve in the normal closed state of the pinch valve in which the tube 75 is compressed between the first pinch part 77 and the second pinch part 87.

In the embodiment of FIG. 16, as a fail-safe the second pinch part 87 can be moved backwards away from the first pinch part 77 (i.e. in the same direction as the direction in which the first pinch part 77 is moved to close the valve) to uncompress the tube 75 so that fluid can flow through the tube despite the first pinch part 77 being in the closed position.

Figure 16B:
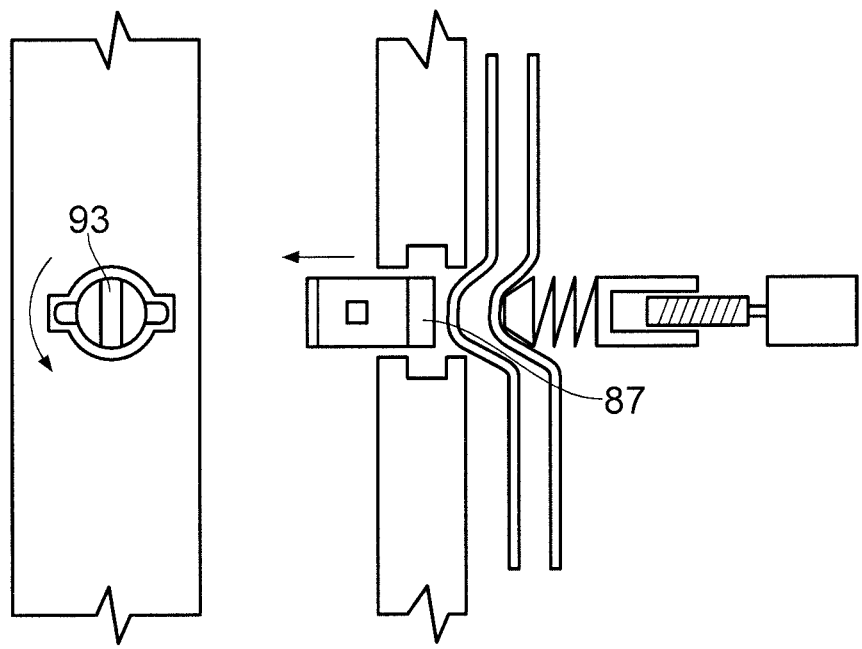

This is achieved by the second pinch part 87 being a cylindrical part that can be housed in a cylindrical channel through a side wall of the pinch valve in a first state shown in FIG. 16(a), and that can be removed from the channel in a second state shown in FIG. 16(b). When the second pinch part 87 is removed from the channel as shown in FIG. 16(b), the tube 75 is able to move sideways into the space previously occupied by the second pinch part 87 so that it is no longer compressed, or is less compressed, so that fluid can flow through the valve.

A safety mechanism is provided to prevent the second pinch part 87 accidentally being removed from the channel to allow fluid to flow through the valve. Specifically, the second pinch part 87 is rotatable within the channel between a first rotational position in which the second pinch part 87 engages the channel so that it cannot be removed from the channel, and a second rotational position in which the second pinch part 87 does not engage the channel and can be removed from the channel.

As shown in FIG. 16, the second pinch part 87 has side protrusions 90, or wings, which engage corresponding recesses in the channel when the second pinch part 87 is in the first rotational position to prevent movement of the second pinch part 87 along the channel when the second pinch part 87 is in the first rotational position.

As shown in FIG. 16, part of the second pinch part 87 protrudes from the housing of the pinch valve to provide an actuator 93 that a user can use to rotate the second pinch part 87 and to pull the second pinch part 87 out of the channel. For example, the end face of the actuator 93 may have a slot or groove that can be engaged, e.g. by a tool or coin, to rotate the second pinch part 87.

The invention claimed is:

1. A urinary drainage system comprising:
   a pinch valve including:
      a tube attachment part for attaching the pinch valve to a tube of the urinary drainage system so that the tube is received in a tube receiving region of the pinch valve;
      a first pinch part and a second pinch part having the tube receiving region therebetween, wherein the first pinch part is moveable towards the second pinch part for compressing a tube received in the tube receiving region against the second pinch part;
   and
      an actuator operable to move the first pinch part;
      wherein the tube attachment part is openable so that the tube is receivable in the tube receiving region, and closeable so that the tube is retained in the tube receiving region; and one of a urinary catheter having a tube to which the pinch valve is attached by the tube attachment part with the tube of the urinary catheter received in the tube receiving region and a urine collector having a tube to which the pinch valve is attached by the tube attachment part with the tube of the urine collector received in the tube receiving region;

wherein the tube has a reduced wall-thickness portion having a reduced wall-thickness; and the reduced wall-thickness portion is received in the tube receiving region.

2. The urinary drainage system according to claim 1, wherein the tube attachment part has a moveable part that is moveable to open and close the tube attachment part.

3. The urinary drainage system according to claim 1, wherein the pinch valve comprises tube engaging means configured to engage a tube received in the tube receiving region.

4. The urinary drainage system according to claim 3, wherein the tube engaging means comprises opposed first and second engaging parts configured to engage the tube therebetween.

5. The urinary drainage system according to claim 1, wherein:

the tube has a locator attached thereto for locating the pinch valve on the tube; and the pinch valve has a locator engaging part for engaging the locator to locate the pinch valve on the tube.

6. The urinary drainage system according to claim 1, wherein the pinch valve comprises a biasing element between the actuator and the first pinch part, wherein the biasing element is compressed when the first pinch part compresses a tube against the second pinch part.

7. The urinary drainage system according to claim 1, wherein the pinch valve comprises a release mechanism operable by a user of the pinch valve to move the second pinch part relative to the first pinch part.

8. The urinary drainage system according to claim 1, wherein:

the actuator comprises a valve shuttle;

the actuator is operable to cause linear movement of the valve shuttle; and the first pinch part is coupled to the valve shuttle so that linear movement of the valve shuttle causes linear movement of the first pinch part.

9. The pinch valve according to claim 8, wherein:

the actuator comprises a screw part having an external screw thread;

the actuator is operable to rotate the screw part;

the valve shuttle has an internal screw thread engaged with the external screw thread of the screw part; and the valve shuttle is prevented from rotating with the screw part, so that rotation of the screw part causes linear movement of the valve shuttle.

10. The urinary drainage system according to claim 1, wherein the actuator is an electrically powered actuator and wherein the pinch valve comprises a controller for controlling operation of the actuator.

11. The urinary drainage system according to claim 1, wherein the pinch valve according to claim 1, wherein the actuator is manually operable, and wherein the pinch valve comprises a magnetic switch for causing the actuator to operate, wherein the magnetic switch can be activated by the user bringing a magnet close to the magnetic switch.

* * * * *